US007488576B2

(12) United States Patent
Kelsoe, Jr. et al.

(10) Patent No.: US 7,488,576 B2
(45) Date of Patent: Feb. 10, 2009

(54) METHODS FOR DIAGNOSIS AND TREATMENT OF PSYCHIATRIC DISORDERS

(75) Inventors: John R. Kelsoe, Jr., Del Mar, CA (US); Thomas B. Barrett, La Jolla, CA (US); Alexander B. Niculescu, III, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 279 days.

(21) Appl. No.: 10/332,159

(22) PCT Filed: Jul. 6, 2001

(86) PCT No.: PCT/US01/21453

§ 371 (c)(1), (2), (4) Date: Jun. 16, 2003

(87) PCT Pub. No.: WO02/04677

PCT Pub. Date: Jan. 17, 2002

(65) Prior Publication Data

US 2004/0053257 A1    Mar. 18, 2004

Related U.S. Application Data

(60) Provisional application No. 60/216,263, filed on Jul. 6, 2000.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ................. 435/6; 435/91.1; 435/91.2; 536/24.3

(58) Field of Classification Search ............. None
See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,965,188 | A | 10/1990 | Mullis |

FOREIGN PATENT DOCUMENTS

WO    WO 00/50436    * 8/2000

OTHER PUBLICATIONS

Barrett et al; American Journal of Medical Genetics, vol. 96, pp. 494, abstract.*
Barrett et al; Molecular Psychiatry, vol. 8, pp. 546-557, 2003.*
Myles-Worsley et al, American Journal of Medical Genetics, vol. 88, pp. 544-550, 1999.*
Compton et al; abstract from Gastroenteroloty, vol. 112, 1997.*
Singleton et al; Neuroscience Letters, vol. 234, pp. 19-22; 1997.*
Hacker et al; Gut, 1997, vol. 40, pp. 623-627.*
Pennisi, Science, 1998; 281 (5384):1787-1789.*
Niculescu et al; Physiol. Genomics, vol. 4, pp. 83-91, 2000.*
Calabrese et al; Genomics, vol. 23, pp. 286-288, 1994.*
Blast analysis of chromosome 22 sequence from Sanger center (Jan. 12, 1999) with SEQ ID No: 1.*
Willner "Dopaminergic Mechanisms in Depression and Mania," in *Psychopharmacology: The Fourth Generation of Progress*, Bloom and Kupfer (eds.), Raven Press, NY, 1995, Chapter 80, p. 921.
Berrettini (2000) "Susceptibility Loci for Bipolar Disorder: Overlap with Inherited Vulnerability to Schizophrenia," Biol. Psychiatr. 47:245.
Kelsoe (1999) "Recent Progress in the Search for Genes for Bipolar Disorder," Curr. Psychiatr. Rep. 1:135.
Lipshutz et al. (1999) "High density synthetic oligonucleotide arrays," Nat. Genet. 21:20.
Heimer and Alheid (1991) "Piecing Together the Puzzle of Basal Forebrain Anatomy," Adv. Exp. Med. Biol. 1:295.
Lander and Kruglyak (1995) "Genetic dissection of complex traits: guidelines for interpreting and reporting linkage results," Nat. Genet. 11:241.
Lachman et al. (1996) "Linkage Studies Suggest a Possible Locus of Bipolar Disorder Near the Velo-Cardio-Facial Syndrome Region on Chromosome 22," Am. J. Med. Genet. 74:121.
Kelsoe et al. (1998) "A Genome Survey of Bipolar Disorder Indicates a Susceptibility Locus on Chromosome 22," Am. J. Med. Genet. 81:461, Abstract.
Edenberg et al. (1997) "Initial Genomic Scan of the NIMH Genetics Initiative Bipolar Pedigrees: Chromosomes 3, 5, 15, 16, 17, and 22," Am. J. Med. Genet. 74:238.
Detera-Wadleigh et al. (1999) "A high-density genome scan detects evidence for a bipolar-disorder susceptibility locus on 13q32 and other potential loci on 1q32 and 18p11.2," Proc. Natl. Acad. Sci. USA 96:5604.
Myles-Worsley et al. (1999) "Linkage of a Composite Inhibitory Phenotype to a Chromosome 22q Locus in Eight Utah Families," Am. J. Med. Gente. 88:544.
Pitcher et al. (1998) "G Protein-Coupled Receptor Kinases," Ann. Rev. Biochem. 67:653.
Tiberi et al. (1996) "Differential Regulation of Dopamine D1A Receptor Responsiveness by Various G Protein-coupled Receptor Kinases," J. Biol. Chem. 271:3771.
Arriza et al. (1992) "The G-Protein-coupled Receptor Kinases βARK1 and βARK2 Are Widely Distributed at Synapses in Rat Brain," J. Neurosci. 12:4045.
Garcia-Sevilla et al. (1999) "Up-Regulation of Immunolabled $\alpha_{2A}$-Adrenoceptors, $G_i$ Coupling Proteins, and Regulatory Receptor Kinases in the Prefrontal Cortex of Depressed Suicides," J. Neurochem. 72:282.

(Continued)

*Primary Examiner*—Jehanne S Sitton
(74) *Attorney, Agent, or Firm*—Medlen & Carroll, LLP

(57) ABSTRACT

The present invention provides methods for the diagnosis and treatment of psychiatric disorders. In particular, the present invention provides convergent functional genomics methods for the identification of candidate genes associated with psychiatric disorders such as mania and psychosis, as well as other multi-faceted diseases and syndromes.

6 Claims, 4 Drawing Sheets

OTHER PUBLICATIONS

Ripperger et al., (2000) "Clock, an essential pacemaker component, controls expression of the circadian transcription factor DPB," Genes Dev. 14:679.

Yan et al. (2000) "Distribution and Circadian Expression of dbp is SCN and Extra-SCN Areas in the Mouse Brain," J. Neurosci. Res. 59:291.

Franken et al. (2000) "The Transcription Factor DBP Affects Circadian Sleep Consolidation and Rhythmic EEG Activity," J. Neurosci. 20:617.

Andretic et al. (1999) "Requirement of Circadian Genes for Cocaine Sensitization in *Drosphila*," Science 285:1066.

Kripke et al. (1978) "Circadian Rhythm Disorders in Manic-Depressives," Biol. Psychiatr. 13:335.

Bunney and Bunney (2000) "Molecular Clock Genes in man and Lower Animals: Possible Implications for Circadian Abnormalities in Depression," Neuropsychopharmacol. 22:335

Morissette et al. (1999) "Genome-Wide Search for Linkage of Bipolar Affective Disorders in a Very Large Pedigree Derived from a Homogeneous Population in Quebec Points to a Locus of Major Effect on Chromosome 12q23-q24," Am. J. Med. Genet. 88:567.

Schechter et al. (1994) "Localization of the Squalene Synthase Gene (FDFTI) to Human Chromosome 8p22-p23.1," Genomics 20:116.

Engelberg (1992) "Low serum cholesterol and suicide,"Lancet 339:727.

Kaplan et al. (1997) "Assessing the Observed Relationship between Low Cholesterol and Violence-related Mortality," Ann. NY Acad. Sci. 836:57.

Tozawa et al. (1999) "Embryonic Lethality and Defective Neural Tube Closure in Mice Lacking Squalene Synthase," J. Biol. Chem. 274:30843.

Michikawa and Yanagisawa (1999) "Apolipoprotein E4 isoform-specific actions on neuronal cells in culture," Mech. Ageing Dev. 107:223.

Wetterberg et al. (1998) "Search for Schizophrenia Loci in a Swedish Geographic Isolate," Am. J. Med. Genet. 81:470, Abstract.

Kaufmann et al. (1998) "NIMH Genetics Initiative Millennium Schizophrenia Consortium," Linkage Analysis of African-American Pedigress, Am. J. Med. Genet. 81:282.

Jo et al. (1999) "Characterization of MALS/Velis-1, -2, and -3: a Family of Mammalian LIN-7 Homologs Enriched at Brain Synapses in Association with the Postsynaptic Density-95/NMDA Receptor Postsynaptic Complex," J. Neurosci. 19:4189.

Butz et al. (1998) "A Tripartite Protein Complex with the Potential to Couple Synaptic Vesicle Exocytosis to Cell Adhesion in Brain," Cell 94:773.

Dawson et al. (1995) "Linkage Studied on Bipolar Disorder in the Region of the Darier's Disease Gene on Chromosome 12q23-24.1," Am. J. Med. Genet. 60:94.

Ewald et al. (1995) "A possible locus for manic depressive illness on chromosome 16p13," Psychiatr. Genet. 5:71.

Hwang and Choi (1995) "Induction of Gene Expression of the Catecholamine-Synthesizing Enzymes by Insulin-Like Growth Factor-1," J. Neurochem. 65:1988.

Knusel et al. (1991) "Trophic Actions of IGF-1, IGF-II and Insulin on Cholinergic and Dopaminergic Brain Neurons," Adv. Exp. Med. Biol. 293:351.

Beck et al. (1995) "*Igf1* Gene Disruption Results in Reduced Brain Size, CNS Hypomyelination, and Loss of Hippocampal Granule and Striatal Parvalbumin-Containing Neurons," Neuron 14:717.

Schmidt and Schibler (1995) "Cell Size Regulation, a Mechanism That Controls Cellular RNA Accumulation: Consequences on Regulation of the Ubiquitous Transcription Factors Oct. 1 and NF-Y, and the Liver-enriched Transcription Factor DBP," J. Cell Biol. 128:467.

Bina et al. (2000) "Syndromes Associated with *Homo sapiens* Pol II Regulatory Genes," Prog. Nucl. Acid Res. Mol. Biol. 64:171.

Kandil et al. (1996) "The human gene encoding the heavy chain of the major histocompatibility complex class I-like Fc receptor (FCGRT) maps to 19q13.3," Cytogenet. Cell Genet. 73:97.

Flores et al. (1998) "Long-Lasting Induction of Astrocytic Basic Fibroblast Growth Factor by Repeated Injections of Amphetamine: Blockade by Concurrent Treatment with a Glutamate Antagonist," J. Neurosci. 18:9547.

Rabinovsky et al. (1995) "Regulation of Tyrosine Hydroxylase Gene Expression in IMR-32 Neuroblastoma Cells by Basic Fibroblast Growth Factor and Ciliary Neurotrophic Factor," J. Neurochem. 64:2404.

Blouin et al. (1998) "Schizophrenia susceptibility loci on chromosomes 13q32 and 8p21," Nat. Genet. 20:70.

Kendler et al. (1996) "Evidence for a Schizophrenia Vulnerability Locus on Chromosome 8p in the Irish Study of High-Density Schizophrenia Families,"Am. J. Psychiatr. 153:1534.

Levinson et al. (1998) "Genome Scan of Schizophrenia," Am. J. Phsychiatr. 155:741.

Lewis et al. (1999) "A Role for HSP27 in Sensory Neuron Survival," J. Neurosci. 19:8945.

Kato et al. (1999) "Responses of Heat Shock Proteins hsp27, α B-Crystallin, and hsp70 in Rat Brain After Kainie Acid-Induced Seizure Activity," J. Neurochem. 73:229.

Detera-Wadleigh et al. (1997) "Initial Genome Scan of the NIMH Genetics Initiative Bipolar Pedigrees: Chromosomes 4, 7, 9, 18, 19, 20, and 21q," Am. J. Med. Genet. 74:254.

Maniatis et al. (1987) "Regulation of Inducible and Tissue-Specific Gene Expression," Science 236:1237-1245.

Voss et al. (1986) "The Role of Enhancers in the Regulation of Cell-Type-Specific Transcriptional Control," Trends Biochem. Sci. 11:287-289.

Dijkema et al. (1985) "Cloning and Expression of the Chromosomal Immune Interferon Gene of the Rat, " EMBO J. 4(3):761-767.

Uetsuki et al. (1989) "Isolation and Characterization of the Human Chromosomal Gene for Polypeptide Chain Elongation Factor-1α," J. Biol. Chem. 264(10):5791-5798.

Kim et al. (1990) "Use of the Human Elongation Factor 1α Promoter as a Versatile and Efficient Expression System," Gene 91:217-223.

Mizushima and Nagata (1990), "pEF-BOS, a Powerful Mammalian Expression Vector," Nucl. Acids. Res. 18(17):5322.

Gorman et al. (1982) "The Rous Sarcoma Virus Long Terminal Repeat is a Strong Promoter when Introduced into a Variety of Eukaryotic Cells by DNA-Mediated Transfection," Proc. Natl. Acad. Sci. USA 79:677-6781.

Boshart et al. (1985) "A Very Strong Enhancer is Located Upstream of an Immediate Early Gene of Human Cytomegalovirus," Cell 41:521-530.

Sambrook et al., *Molecular Cloning: A Laboratory Manual*, 2nd ed., Cold Spring Harbor Laboratory Press, New York [1989], pp. 16.7-16.8.

Anderson and Young, "Quantitative Filter Hybridization," in *Nucleic Acid Hybridization*, 1985.

Kacian et al. (1972) "A Replicating RNA Molecule Suitable for a Detailed Analysis of Extracellular Evolution and Replication," Proc. Natl. Acad. Sci USA 69(10):3038-3042.

Chamberlin et al. (1970) "New RNA Polymerase from *Escherichia coli* Infected with Bacteriophage T7," Nature 228:227-231.

Wu and Wallace (1989) "The Ligation Amplification Reaction (LAR)—Amplification of Specific DNA Sequences Using Sequential Rounds of Temple-Dependent Ligation," Genomics 4:560-569.

Sambrook et al., *Molecular Cloning: A Laboratory Manual*, 2nd ed., Cold Spring Harbor Press, NY, pp. 9.31-9.58 [1989].

Sambrook et al., *Molecular Cloning: A Laboratory Manual*, 2nd ed., Cold Spring Harbor Press, NY, pp. 7.39-7.52 [1989].

Sambrook et al., *Molecular Cloning: A Laboratory Manual*, 2nd ed., Cold Spring Harbor Press, NY, pp. 16.9-16.15 [1989].

Nickerson et al. (19997) "PolyPhred: automating the detection and genotyping of single nucleotide substitutions using fluorescence-based resequencing," Nucl. Acids Res. 25:2745-2751.

Terwillinger (1995) "A Powerful Likelihood Method for the Analysis of Linkage Disequilibrium between Trait Loci and One or More Polymorphic Marker Loci," Am. J. Hum. Genet. 56:777-787.

Schaid (1999) "Likelihoods and *TDT* for the Case-Parents Design," Genet. Epidermiol. 16:250-260.

Dautzenberg et al. (2001) "GRK3 mediated desensitization of CRF$_1$ receptors: a potential mechanism regulating stress adaptation," Am. J. Physiol.

Dautzenberg and Hauger (2001) "G-protein-coupled receptor kinase 3- and protein kinase C-mediated desensitization of the PACAP receptor type 1 in human Y-79 retinoblastoma cells," Neuropharmacology 40:394-407.

Mulchahey et al. (1999) "Coordinate and Divergent Regulation of Corticotropin-Releasing Factor (CRF) and CRF-Binding Protein Expression in an Immortalized Amygdalar Neuronal Cell Line," Endocrinology 140:251-259.

Oppermann et al. (1996) "Monoclonal antibodies reveal specificity among G-protein-coupled receptor kinases," Proc. Natl. Acad. Sci. USA 93:7649-7654.

Penn and Benovic (1994) "Structure of the Human Gene Encoding the β-Adrenergic Receptor Kinase," J. Biol. Chem. 269:14924-14930.

Ramos-Ruiz et al. (2000) "Analysis of the Human G Protein-Coupled Receptor Kinase 2 (GRK2) Gene Promoter: Regulation by Signal Transduction Systems in Aortic Smooth Muscle Cells,"Circulation 101:2038-2089.

Benovic et al. (1991) "cDNA cloning and chromosomal localization of the human β-adrenergic receptor kinase," FEBS Lett. 283:122-126.

Gruber et al. (1997) "POU Domain Factors of the Bm-3 Class Recognize Functional DNA Elements Which Are Distinctive, Symmetrical, and Highly Conserved in Evolution," Mol. Cell. Biol. 17:2391-2400.

Trieu et al. (1999) "Autoregulatory Sequences are Revealed by Complex Stability of the Mouse *brn*-3.0 Locus," J. Neurosci. 19:6549-6558.

Carter (1990) "Temporally Defined Induction of c-fos in the Rat Pineal," Biochem. Biophys. Res. Commun. 166:589-594.

Kelsoe et al. (1989) "Re-evaluation of the linkage relationship between chromosome IIp loci and the gene for bioplar affective disorder in the Old Order Amish," Nature 342:238-243.

Yu et al., (1999) "Psychological States and Lymphocyte β-Adrenergic Receptor Responsiveness," Neuropsychopharma. 21:147-152.

Wright et al. (1984) "β-Adrenocepter binding defects in cell lines from families with manic-depressive disorder," Ann. Hum. Genet. 48:201-214.

Deckert et (1998) "Adenosine A 1 receptor and bipolar affective disorder: systematic screening of the gene and association studies," Am. J. Med. Genet. 81:18-23.

Sobell et al. (1993) "Novel association approach for determining the genetic predisposition to schizophrenia: case control resource and testing of a candidate gene," Am. J. Med. Genet. 48:28-35.

Carlsson et al. (2000) "Total RNA and array-based expression monitoring," Nature Biotech. 18:579.

Williams et al. (2002) "Genome scans and microarrays: converging on genes for schizophrenia?" Genome Biol. 3:1011.1-1011.5.

McKenzie et al. (1998) "Parallel Molecular Genetic Analysis," Euro. J. Human Genet. 6:417-429.

Barrett et al. (2003) "Evidence that a single nucleotide polymorphism in the promoter of the G protein receptor kinase 3 gene is associated with bipolar disorder," Molec. Psychia. 8:546-557.

Compton and Nemeroff, "Depression and Bipolar Disorder," in Dale and Federman (eds.), Scientific American Medicine, Healtheon/WebMD, NY, Dec. 2003 update.

Ewald et al. (1995) "No evidence of linkage between amnic depressive illness and the dopa decarboxylase gene or nearby region on chromosome 7p, " Psychiatr. Genet. 5:161-169.

Niculescu III et al. (2000) "Identifying a series of candidate genes for mania and psychosis: a convergent functional genomics approach," Physiol. Genomics 4:83-91.

* cited by examiner

Fig. 2

```
gggctgtgcgtgggagagaaacaaagagggaaacaggctatttgatgacagaatcaggctgcttctg      70
caatgacattacagtgaaatatctgaaatttgaccttaactgtatctggtgtcccgttaaccctgtaag    140
ttatggacagaacgttcactcaacgtctagcaacgtctatgctcatgaaatacgtgaccaattcaggtg    210  514a T -> C
aatgaaagggatttaaaaacatTaatttccagctcttaggtcttcctaAgactgctgcgtgtccctacca   280  514b A -> G
ccactccagcctgagtgtcacatggatcctgaatgcggacttgtgtgcacactgtagaaaataagcaac    350  514c T -> G
tgaaaacccaggcaTcggggtggagtgatgatgaaagacaccgagaccgaagatcaggaagctggaaat    420
tcccccagcttcggtttggctgcccctaattgtctctcttgtattgaccgtaaaccctcacctgagtgt    490
gtgctcgcagcagatgctcctcaacacattcaacaccaaactctaaaacctctcacctgagtgtaaggagtggt 560
tctccttctctatttcttcaacacattcaacaccaaactaaaacctctcacctgagtgtaaggagtggt   630
gaccttcttaagcggagagctcttcgcttagcctaagacacgcaacttttccagctctctgttcctaga  700  515c A -> G
cgtcacgcactttgtctgctcagcagagttcatcattacctgctggataggtggacacatgtatttccg    770
accggtagccggaccagagcaggagtttcatcattacctgctggataggtggacacatgtatttccg     840
gggccaccccagactccccggagacctccccataaccctggggttgtgtgggacgtctgtccagttgac   910
cagaggcctcccataaccctggggttgtgtgggacgtctgtccagttgacactgttgagaactgttccgg  980
catcagaggcgcgtggaacctggggcggtggaacgtcggggcagtgaaggaggaggagccgaga       1050
ccgaggggaggggaggagagccgccgagcagtccctcgtgccaccccgagGgagggcgacc          1190  515a G -> A
gtagagacttggtcggagggcgccgccccagaccctcgaaggagcgctgcactgcgactgaccgt       1260
tggacgcgctcccccggaggcgggagcggtgctgcgaccctgcgaccctgcgcgcggcg             1330
gcgcgcgagggggcgggagcgggagcggcgcgcgcgcgcgcgcgcgcctgcgcgcgggcg            1400
cgctagtgggggcgcgcgcgcgggcgcggcgcgcgggggGctgcccgggcggccc              1470  515b G del
ccccaggtcggcgcgcgggcgcgcgcgcgcgcgtccagtccggagtaaccgccgcc                1540
gccgcgcaaagctcgccaacatggcctggaggcctgctgctggccgatgtcagttacctgatgcc       1610
atggagaaga
         ↘ Translation start
```

Fig. 2

SEQUENCE LISTING

<160> NUMBER OF SEQ ID NOS: 1

<210> SEQ ID NO 1
<211> LENGTH: 1620
<212> TYPE: DNA
<213> ORGANISM: Homo sapiens

<400> SEQUENCE: 1

```
gggctgtggc gtgggagaga aaacaaaaga gggaaacagg ctatttgatg acagaatcag     60
gctgcttctg caatgacatt acatgaaata tctgaaattt gaccttaact gtatctggtg    120
ggtcccgtta accctgtaag ttatggacag aacgttcact caaattctag caacgtctag    180
gctcatggaa atacgtgacc aattcaggtg aatgaaaggg attttaaaac attaatttcc    240
agcttaggtc ttcctaagac tgcctgcgtg tcccttacca ccactccagc ctgagtgtca    300
catggatcct gaatgcggac ttgtgtgcac actgtagaaa aataagcaac tgaaaacccc    360
aggcatcggg gtggagtgat gatgaaagac accgagaccg aagatcagga agctggaaat    420
tcccccagc ttcggtgttt gggctgtatc tcgcttttcc acttccctaa atcaccctcg     480
tggtgcgagt gtgctcgcag cagatgctcc ctaattgtct cttgtattga ccgtaaaacc    540
ctaacgacag gaatactctc tctccttcta tttctcaaca ccatttcaac acccaaacta    600
aaacctctca cctgagtgta agggagtggt gaccttctta agcggagagc tcttccatca    660
gagggctccc taagggcatc tctgttccta gccggggagc cgtcacccca ctttgttctg    720
cttagcctaa gacacgcaac tttttccagc ttttactctt cgctgaattc tcacggtggg    780
gttgggggga tgttcaggct caggagcgag gttggggggcc cggcccgctg ggcgctgttc   840
accggtagcc cggaccagag caggagtttc atcattacct gctgggatag gtgggacaca    900
tgtatttccg gggccacccc agacctcccg gaggatgctg attgacactg tccagtttga    960
gaactactgt gtccagggag cagaggcctc cccataaccc cttgggttgt ggacgtctgg   1020
cccagggctt ctctgggtga gcggggcggg catcagagcg cgtggaacct ggggcgggag   1080
gtcgggggcag tgaaggagga ggagaaggag gaggcggaga ccgaggggga gggaggggag   1140
gaggaagagg aggaggagtc cctcgtggcc accccgaggg gagggcgacc gtagagactt   1200
ggtcgggagg cgccggccca gcgaggccgc tgggactgtg cactgagggg cgctgaccgt   1260
tggacgcgcg ctccccgcag accctcgctg aaggagcagg gggcggcgcg cgtgcgcggg   1320
gcgccgggcg gcgcgcgagg gggcggagcg gggaggcgtg ctgcgacccc ggccggctac   1380
agcctgcggc gcgcgcagag cgctagtggg gcgcgcggcg cgcgcgcggg gcggggcgc    1440
gcggagggggg gggctgcccc ggggcggccc cccaggtcg gggcgcggcg ggcggcggcg    1500
gcgggcgcgc gtcccgtcca ggtccggagt aaccgccgcc gccgccgcca aagctcgcca   1560
acatggcgga cctggaggct gtgctggccg atgtcagtta cctgatggcc atggagaaga   1620
```

METHODS FOR DIAGNOSIS AND TREATMENT OF PSYCHIATRIC DISORDERS

This application is a U.S. national entry of International Application No. PCT/US01/21453, filed on Jul. 6, 2001, which claims priority to U.S. Provisional Application Ser. No. 60/216,263, filed Jul. 6, 2000.

This invention was made, in part, with Government support by the National Institutes of Health Grant Number MH47612. The Government has certain rights in the invention.

FIELD OF THE INVENTION

The present invention provides methods for the diagnosis and treatment of psychiatric disorders. In particular, the present invention provides convergent functional genomics and other methods for the identification of candidate genes associated with psychiatric disorders such as mania and psychosis, as well as other multi-faceted diseases and syndromes. In addition, the present invention provides methods and compositions for the screening and identification of therapeutic compounds, as well as genetic and protein-based therapies.

BACKGROUND OF THE INVENTION

In the U.S., major depression ranks first among all causes of disability and second after heart disease as a cause of healthy years lost to premature mortality and disability (See, Hyman and Rudorfer, "Depressive and Bipolar Mood Disorders," in Dale and Federman (eds.), Scientific American Medicine, Healtheon/WebMD, New York, N.Y. [2000]). Indeed, approximately 10 percent of the population experiences at least one depressive episode that would benefit from treatment, while 5 percent would be classified as having severe and disabling symptoms of depression (See, Hyman and Rudorfer, supra).

While the prevalence of unipolar depression (major depression) in the U.S. is 5-10 percent, with women having approximately a two-fold greater risk than men, the prevalence of bipolar disorder (manic-depressive illness) is approximately 1 percent, is less variable, and affects men and women equally (See, Hyman and Rudorfer, Supra). There is a strong familial association for unipolar, as well as bipolar disorder. For example, the familial nature of bipolar disorder is associated with a 5 to 10-fold increased risk in first-degree relatives above the 1 percent risk in the general population (See, Hyman and Rudorfer, supra). Bipolar disorder often begins in young adulthood (e.g., second or third decade of life), although childhood onset is increasingly being recognized. Late onset is less common, but can even occur in the elderly. In rare cases, patients may have only a single manic episode. However, the vast majority of patients have recurrent episodes of illness, with the rate of cycling between mania and depression varying widely among individuals, and the episodes becoming more frequent with age. Between episodes of depression and mania, the majority of patients are symptom-free, although as many as one-third of patients exhibit residual symptoms.

Patients affected by bipolar disorder have had at least one manic or hypomanic (mild mania) episode. However, at the time of diagnosis, they may never have had a depressive episode, according to the DSM-IV criteria. The diagnosis is supported by family history data and observational studies. According to the DSM-IV, patients with full manias and depression are indicated as having "bipolar I disorder," while patients with hypomanias and depressions are described as having "bipolar II disorder." Onset of episodes tends to be acute, with symptoms developing over days to weeks. The depressive episodes of bipolar patients are indistinguishable from those of patients with unipolar disorder. Thus, misdiagnosis of bipolar disorder is common. Indeed, as many as 40 percent of bipolar patients are initially misdiagnosed (See, Hyman and Rudorfer, supra). It is also not uncommon for clinicians to misclassify bipolar patients as depressed or schizophrenic on the basis of their mental status. However, it is important to make a proper diagnosis, as administration of some drugs can seriously worsen the patient's clinical picture.

In addition to the problems associated with diagnosis, treatment of bipolar disorder can be problematic. Indeed, it has been estimated that 5 percent of patients experience chronic unremitting symptoms despite treatment (See, Hyman and Rudorfer, supra). Mania requires prompt treatment because it can rapidly worsen, resulting in poor judgment that endangers interpersonal relationships, jobs, and finances. Management is founded upon medication, provision of a low-stimulation environment, and protecting the patient from undertaking potentially harmful activities. Initial management of acute mania is often best accomplished through hospitalization. Thus, the management of bipolar disorder can be expensive, intrusive, and difficult. In addition, despite the now routine use of maintenance treatment for bipolar disorder, up to 90 percent of patients experience at least one relapse within 5 years of their original diagnosis (See, Hyman and Rudorfer, supra). Thus, it is clear that improved methods and compositions for the diagnosis and treatment of psychiatric diseases such as bipolar disorder are needed.

SUMMARY OF THE INVENTION

The present invention provides methods for the diagnosis and treatment of psychiatric disorders. In particular, the present invention provides convergent functional genomics methods for the identification of candidate genes associated with psychiatric disorders such as mania and psychosis, as well as other multi-faceted diseases and syndromes. In some particularly preferred embodiments, the present invention provides methods and compositions for the diagnosis and prognosis of psychiatric disorders. In alternative particularly preferred embodiments, the present invention provides methods and compositions for screening and identification of compounds with therapeutic value for treatment of psychiatric disorders, including but not limited to bipolar disorder, schizophrenia, schizoaffective disorder, psychosis, depression, stimulant abuse, alcoholism, panic disorder, generalized anxiety disorder, attention deficit disorder, post-traumatic stress disorder, and Parkinson's disease. In addition, the present invention provides methods and compositions for the prediction and assessment of patient responses to therapeutic agents, as well as for monitoring patient condition/response to treatment over time. The present invention further provides genes and proteins associated with psychiatric disorders, as well as methods and compositions for gene therapy of psychiatric disorders. In still additional embodiments, the present invention provides methods and compositions for protein-based therapy.

In one embodiment, the present invention provides convergent functional genomics methods for the identification of candidate genes associated with psychiatric disorders. In particularly preferred embodiments, the methods involve determining changes in gene expression between treated and untreated tissues by using a quantitative hybridization assay and oligonucleotide gene chips or microarrays. In some preferred embodiments, repressed or induced genes are scored as mapping to a psychiatric disorder linkage region if these genes or their human homologues are located within about 10 cM of a putative psychiatric disorder marker. In one embodiment, treatment consists of amphetamine administration, while in others treatment consists of methamphetamine, cocaine or methylphenidate. This invention is not limited to these treatments as any other direct or indirect dopamine agonist is suitable for use in the present invention. In a preferred embodiment, the psychiatric disorder of this method is bipolar disorder, which is also known as manic-depressive illness. In related embodiments, the psychiatric disorder is selected from the group consisting of unipolar depression, major depression, schizophrenia, schizoaffective disorder and attention deficit disorder.

The present invention also provides methods for diagnosing bipolar disorder, identifying individuals at risk for bipolar disorder, and assessing bipolar disorder prognosis by detecting sequence variation in a fragment or fragments of a patient's G protein-coupled receptor kinase 3 (GRK3) gene. In a preferred embodiment, the GRK3 gene fragment comprises the promoter. In some embodiments, the sequence variation comprises a SNP located approximately 1330 bp upstream of the GRK3 start codon, while in other embodiments, the sequence variation comprises a SNP positioned upstream of the GRK3 start codon at various locations including about 1306 bp, about 1197 bp, about 901 bp, about 383 bp, and about 110 bp. The present invention also provides methods for predicting treatment response. In one preferred embodiment, the present invention provides methods for predicting a subject's response to an antidepressant, wherein the response is selected from the group consisting of hypomania, mania and psychosis.

The present invention also provides methods for screening compounds that alter the expression of psychiatric genes comprising: providing a plurality of cells comprising psychiatric genes, standard medium, medium containing at least one dopamine agonist, and at least one test compound; incubating a first aliquot of cells in standard medium containing at least one test compound; incubating a second aliquot of cells in medium containing at least one dopamine agonist and at least one test compound; quantitating expression of the psychiatric genes in the first and second aliquots of cells; and comparing expression of the psychiatric genes in the first and second aliquots of cells. In a preferred embodiment, the cells of the invention are neurally derived cells, while in other embodiments, lymphoblastoid cell lines or other types of cells find use in the present invention. In some embodiments, quantitation of gene expression is achieved using a technique selected from the group consisting of Northern blots, RT-PCR, Western blots, enzyme-linked immunosorbent assays, fluorescence immunoassays, radioimmunoassays, luciferase assays, fluorescence assays, and flow cytometry. In some preferred embodiments, the psychiatric gene is a psychogene, while in other embodiments it is a psychosis-suppressor gene. In a particularly preferred embodiment, the psychiatric gene is selected from the group consisting of the G protein-coupled receptor kinase 3 (GRK3) gene, the D-box binding protein (DBP) gene, the farnesyl-diphosphate farnesyltransferase (FDFT1) gene, the vertebrate LIN7 homolog 1 (VELI1) gene, the sulfotransferase 1 A1 (SULT1A1) gene and the insulin-like growth factor 1 (IFG1) gene.

In particular the present invention provides methods for the identification of genes associated with psychiatric disorders, comprising the steps of: providing test antisense cRNA and control antisense cRNA; hybridizing the test antisense cRNA and the control antisense cRNA to a microarray comprising at least two nucleic acids; measuring the hybridization of the test antisense cRNA and the control antisense cRNA to the nucleic acids; comparing the hybridization of the test antisense cRNA with the hybridization of the control antisense cRNA to provide a hybridization score; determining whether the hybridization score indicates the test antisense cRNA represents a gene with altered expression; and determining whether the gene maps to a psychiatric disorder linkage region. In preferred embodiments, the identified gene is a human homologue. In another preferred embodiment, the gene maps to within about 10 cM of a putative marker associated with a psychiatric disorder, while in another embodiment, the putative marker associated with a psychiatric disorder has been identified as such in human genetic studies. In some embodiments, the gene with altered expression is selected from the group consisting of induced genes and repressed genes. Additionally in some embodiment the microarray comprises at least one gene chip. Moreover, the hybridized test antisense cRNA and the control antisense cRNA are labelled in some embodiments and the label is selected from the group consisting of fluorescent labels, luminescent labels, enzyme labels, and radioactive labels. In particularly preferred embodiments, the psychiatric disorder is selected from the group consisting of bipolar disorder, manic-depressive illness, unipolar depression, major depression, schizophrenia, schizoaffective disorder, and attention deficit disorder. In the method of the present invention the test antisense cRNA is obtained from an animal treated with a dopamine agonist and the control antisense cRNA is obtained from an animal not treated with a dopamine agonist in some embodiments. In other embodiments, the dopamine agonist is selected from the group consisting of amphetamine, methamphetamine, cocaine and methylphenidate.

The present invention also provides methods for diagnosing bipolar disorder comprising detecting sequence variation in at least one fragment of a G protein-coupled receptor kinase 3 (GRK3) gene obtained from a subject. In some embodiments, the detecting comprises nucleotide sequencing. In particularly preferred embodiments, the subject is an individual at risk of developing bipolar disorder. In other preferred embodiments, the fragment of GRK3 gene comprises the promoter. Additionally, the present invention provides methods wherein the sequence variation is selected from the group consisting of: a thymine to cytosine transition at approximately 1330 bp upstream of the translation start site of the GRK3 gene; an adenine to guanine transition at approximately 1306 bp upstream of the translation start site of the GRK3 gene; a thymine to guanine transversion at approximately 1197 bp upstream of the translation start site of the GRK3 gene; an adenine to guanine transition at approximately 901 bp upstream of the translation start site of the GRK3 gene; a guanine to adenine transition at approximately 383 bp upstream of the translation start site of the GRK3 gene; and a guanine deletion at approximately 110 bp upstream of the translation start site of the GRK3 gene. In one preferred embodiment, the sequence variation is predictive of a subject's response to an antidepressant, wherein the response is selected from the group consisting of hypomania, mania and psychosis.

The present invention also provides methods for screening compounds that alter expression of at least one psychiatric gene, comprising the steps of: providing a plurality of cells comprising psychiatric genes, standard medium, medium containing at least one dopamine agonist, and at least one test compound; incubating a first aliquot of the cells with the standard medium and the at least one test compound; incubating a second aliquot of the cells with the medium containing at least one dopamine agonist and the at least one test compound; quantitating the expression of the psychiatric genes in the first aliquot and quantitating the expression of the psychiatric genes in the second aliquot; and comparing the expression of the psychiatric genes in the first aliquot with the expression of the psychiatric genes in the second aliquot In preferred embodiments, the psychiatric genes are selected from the group consisting of psychogenes and psychosis-suppressor genes. In some embodiments, the method for quantification is selected from the group consisting of Northern blots, RT-PCR, Western blots, enzyme-linked immunosorbent assays, fluorescence immunoassays, radioimmunoassays, luciferase assays, fluorescence assays, and flow cytometry. In particularly preferred embodiments, the psychiatric genes are selected from the group consisting of the G protein-coupled receptor kinase 3 (GRK3) gene, the D-box binding protein (DBP) gene, the farnesyl-diphosphate farnesyltransferase (FDFT1) gene, the vertebrate LIN7 homolog 1 (VELI1) gene, the sulfotransferase 1 A1 (SULT1A1) gene, and the insulin-like growth factor 1 (IFG1) gene.

DESCRIPTION OF THE FIGURES

FIG. 2 shows the SNPs detected in the 5' end of the GRK3 gene (SEQ ID NO:1), relative to the start codon.

DESCRIPTION OF THE INVENTION

Figure 1:
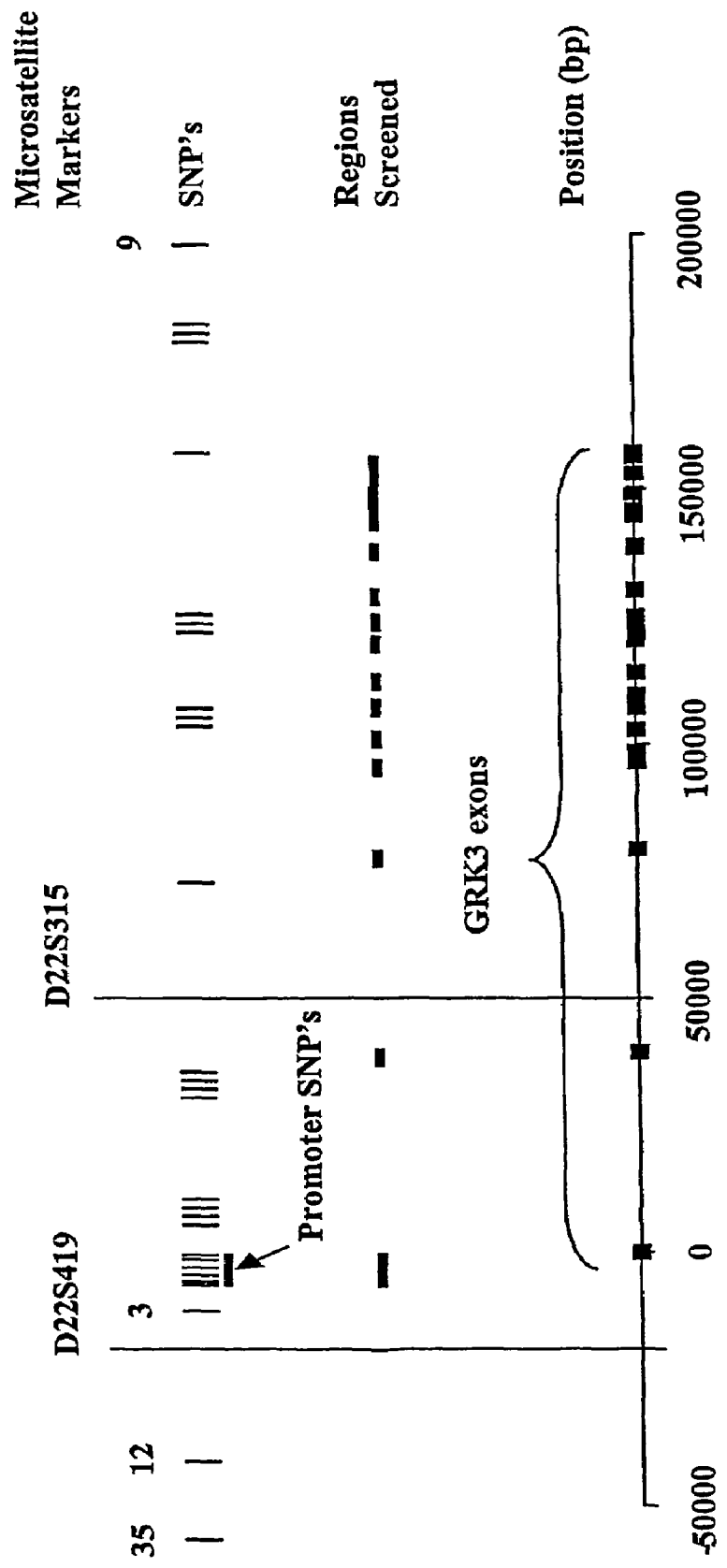
FIG. 1 shows the location of the single nucleotide polymorphisms (SNPs) detected upon screening fragments of G protein-coupled receptor kinase 3 (GRK3) genomic DNA from subjects with bipolar disorder.

The present invention provides methods for the diagnosis and treatment of psychiatric disorders. In particular, the present invention provides convergent functional genomics methods for the identification of candidate genes associated with psychiatric disorders such as mania and psychosis, as well as other multi-faceted diseases and syndromes. In particularly preferred embodiments, the present invention provides methods and compositions for the diagnosis and prognosis of psychiatric disorders. In particularly preferred embodiments, the present invention provides methods and compositions for the screening and identification of compounds with therapeutic value for treatment of psychiatric disorders, including but not limited to bipolar disorder, schizophrenia, schizoaffective disorder, psychosis, depression, stimulant abuse, alcoholism, panic disorder, generalized anxiety disorder, attention deficit disorder, post-traumatic stress disorder, and Parkinson's disease. In addition, the present invention provides methods and compositions for the assessment of patient responses to therapeutic agents, as well as for monitoring patient condition/response to treatment over time. The present invention further provides methods and compositions for gene therapy of psychiatric disorders. In still additional embodiments, the present invention provides methods and compositions for protein-based therapy. For ease in reading, the following Description of the Invention is divided into several sections: I. Convergent Functional Genomics; II. Psychogenes and Psychosis-Suppressor Genes; and III. Cell Culture Methods.

I. Convergent Functional Genomics

Stimulant administration in man mimics many of the signs and symptoms of psychiatric disorders. For example, it is intended that the approach of the present invention will find use with various animal models and associations with mapping and identification of susceptibility genes that are involved in numerous psychiatric and other diseases. However, it is not intended that the present invention be limited to the administration of any particular stimulant or indeed, any other compound. Nor is it intended the present invention be limited to any particular animal model or any particular disease.

In specific, the association of single dose amphetamine treatment in humans, which is known to reproduce some of the core symptoms of mania, including increased energy, euphoria, irritability, racing thoughts, rapid speech, hyperactivity, decreased need for sleep, and psychomotor agitation was utilized. Chronic treatment frequently results in psychotic symptoms that resemble psychotic mania or the positive symptoms of schizophrenia. These clinical phenomena are consistent with a large body of data that indicate a role for dopamine in mania and psychosis (Wilner, in *Psychopharmacology: The Fourth Generation of Progress*, Bloom and Kupfer (eds.), Raven Press, New York, [1995], page 921). Attempts to map genes for these disorders by positional cloning have yielded some recent successes, with about 20 genomic regions being implicated by linkage studies, many of which are found in studies of both bipolar disorder and schizophrenia (See, Berrettini, *Biol. Psychiatr.* 47:245 [2000]; and Kelsoe, *Curr. Psychiatr. Rep.* 1:135 [1999]).

One of the major difficulties in fine mapping and identification of susceptibility genes for these and other complex genetic disorders is the length of the linkage peaks, which are typically 20 cM or greater. Microarray technologies provide an approach that is capable of simultaneously examining the expression of thousands of genes. Thus, observing changes in gene expression in an amphetamine treatment animal model of mania and psychosis, as well as mapping the genes within these linkage peaks has provided good candidates for disease susceptibility genes during the development of the present invention. This approach, referred to herein as "convergent functional genomics" provides methods to identify any number of candidate genes for psychiatric and other disorders. Indeed, this approach was used during the development of the present invention to identity several positional candidate genes for psychiatric disorders.

In experiments conducted during the development of the present invention, the rat animal model was used. This model is commonly accepted by those in the art for experiments involving psychiatric disorders. In some experiments, rats were treated with a single dose of methamphetamine (4 mg/kg) and sacrificed 24 hours later. This timepoint was chosen as that most likely to detect changes of relevance to mania and psychosis. It was hypothesized that at 24 hours, most short term gene induction relevant to acute intoxication and behavioral activation would have subsided. Furthermore, 24 hours after a single moderate to high dose, animals already exhibited a sensitized response to a second amphetamine challenge. As mania and psychosis are typically chronic processes in man, more persistent gene changes are more likely to be central to pathophysiological mechanisms. Gene expression was examined in the prefrontal cortex and amygdala, using the Afymetrix U34A GeneChip, which interrogates approximately 7,000 known genes and 1,000 ESTs (expressed sequence tags) using an oligonucleotide nicroarray (See, Lipshutz et al., *Nat. Genet.* 21:20 [1999]). These brain regions were chosen based on the extensive literature that highlights their central role in cognition and emotion (See e.g., Heimer and Alheid, *Adv. Exp. Med. Biol.* 1:295 [1991]).

A two-fold increase or decrease in expression was chosen as a conventional empirical cut-off. Thus, at least a two-fold change in each of two independent animal experiments was used to select those genes with the most robust and reproducible change in expression. In each experiment, pooled tissues from three methamphetamine-treated and three control rats were used. In these analyses, standard default settings of the Affymetrix GeneChip Expression Algorithm were used. A gene had to be called "Present" and "Changed," in at least one out of two experiments and had to have an Average Difference Change greater than 50, as well as a fold change greater than 2 in two out of two experiments. Genes meeting this criteria are summarized in Table 1, for the prefrontal cortex (PFC) and Table 2, for the amygdala (AMY). The genes that were induced more than two-fold in both experiments were also identified by their GenBank accession numbers, as indicated in Tables 1 and 2. A gene was scored as mapping to a linkage region for either schizophrenia (S) or bipolar disorder (B) if its human homologue mapped to within 10 cM of a marker for which at least suggestive evidence of linkage had been reported.

The chromosomal locations of the human homologues of these genes were then compared with published linkage reports for bipolar disorder and schizophrenia, as well as data generated during the development of the present invention to cross-validate the results and identify high-probability candidate genes. The human homologues and human chromosomal map locations were determined using the NCBI database. GeneCard (Weizmann Institute), a comprehensive database containing all of the various information available regarding known genes and their functions was also used for each gene identified in the screen. Genes were considered to be positional candidates (i.e., close to a genomic hotspot) if they mapped to within 10 cM of a marker for which there was at least one report of suggestive evidence of linkage (Lander and Kruglyak, *Nat. Genet.* 11:241 [1995]). The Marshfield integrated linkage map was used as a reference for genetic location. As shown in Tables 1 and 2, eight of these genes met the criteria used in the analyses. It was also noted that a number of interesting genes were very narrowly positioned below this threshold. An indication of the specificity of the result is that GRK2, a close homologue of GRK3, demonstrated no change in expression in either experiment (fold changes of 1.1 and 1.0 in two experiments).

TABLE 1

Candidate Genes Reproducibly Induced in the Prefrontal Cortex (PFC)

| Accession # Rat/Human | Gene Symbol | Description | Fold Induction | Human Chromosomal Location | Linkage Region |
|---|---|---|---|---|---|
| M87855/NM_005160 | GRK3 | G protein-coupled receptor kinase 3 | 14.2 | 22q11 | B |
| J03179/U48213 | DBP | D-box binding protein | 7.0 | 19q13.3 | B |
| M95591/X69141 | FDFT1 | Farnesyl-diphosphate farnesyltransferase | 2.9 | 8p23.1-p22 | S |
| AF090134/AF173081 | MALS-1 | Vertebrate LIN7 homolog 1 | 2.9 | 12q21.3 | B |

TABLE 2

Candidate Genes Reproducibly Induced in the Amygdala (AMY)

| Accession # Rat/Human | Gene Symbol | Description | Fold Induction | Human Chromosomal Location | Linkage Region |
|---|---|---|---|---|---|
| AA799479/AF038406 | NDUFS8 | NADH-coenzyme Q reductase | 20.8 | 11q13 | |
| L19998/L19999 | SULT1A1 | Sulfotransferase 1A1 | 4.3 | 16p12.1-p11.2 | B |
| AB017711/Z27113 | POLR2F | RNA polymerase II polypeptide F | 3.9 | 22q13.1 | B, S |
| X14323/U12255 | FCGRT | IgG Fc receptor transporter alpha | 3.2 | 19q13.3 | B |
| M81183/X57025 | IGF1 | Insulin-like growth factor I | 3.0 | 12q22-q24.1 | B |
| AA998683/(AJ224874) EST[1] | HSPB1 | Heat-shock protein 27 | 2.8 | 7q22.1 | |
| S62933/U05012 | NTRK3 | Neurotropin receptor 3 | 2.7 | 15q25 | |
| X59249/L77730 | ADORA3 | Adenosine receptor A3 | 2.7 | 1p21-p13 | |

TABLE 2-continued

Candidate Genes Reproducibly Induced in the Amygdala (AMY)

| Accession # Rat/Human | Gene Symbol | Description | Fold Induction | Human Chromosomal Location | Linkage Region |
|---|---|---|---|---|---|
| U64689/U69140 | FEZ2 | Fasciculation and elongation protein zeta 2 (Zygin II) | 2.3 | 2p22 | |

[1] The putative human homologue for this EST.

For six of the eight genes identified that met the criteria, it is contemplated that these genes have a role in the pathophysiology associated with disease. These six genes implicated by a convergence of data from both amphetamine response and clinical linkage studies represent compelling and novel candidates for disease susceptibility loci. Their map locations and contemplated roles in psychiatric disease are discussed in greater detail below. However, an understanding of the mechanism(s) involved in these genes is not necessary in order to use the present invention. Nonetheless, it is also not intended that the present invention be limited to any particular mechanism(s). It is contemplated that these genes will find use in various assay and analytical systems, including but not limited to the convergent functional genomics described herein, as well as cell culture and other testing systems (e.g., for gene and protein-based therapies, drug development, etc.).

A. G Protein-Coupled Receptor Kinase 3 (GRK3)

The GRK3 gene maps to human chromosome 22q11, and is also referred to as "beta adrenergic receptor kinase 2" (BARK2). This region has been implicated in bipolar disorder by the present inventors and others (See e.g., Lachman et al., *Am. J Med. Genet.* 74:121 [1996]; Kelsoe et al., *Am. J Med. Genet.* 81:461 [Abstract] [1998]; Edenberg et al., *Am. J Med. Genet.* 74:238 [1997]; and Detera-Wadleigh et al., *Proc. Natl. Acad. Sci. USA* 96:5604 [1999]). Indeed, 22q yielded the highest lod scores of any chromosomal region in the genome survey utilized during development of the present invention. Consistent with many findings in this field, this linkage peak was broad and spanned nearly 20 cM. One of the highest lod scores in this region was 2.2 at D22S419, which maps to within 40 kb of GRK3. This marker is also quite close to the markers identified in the two other independent positive linkage reports for 22q in bipolar disorder. A marker within the GRK3 gene, D22S315, has also been implicated in a study of eye tracking and evoked potential abnormalities in schizophrenia (See, Myles-Worsley et al., *Am. J. Med. Genet.* 88:544 [1999]).

The known physiological role of GRK3 in desensitization of receptors and its map location make it one of the more interesting candidates identified during the development of the present invention. In the continuing presence of high agonist concentrations, G protein-coupled receptor (GPCR) signaling is rapidly terminated by a process termed "homologous desensitization." Homologous desensitization of many agonist-activated GPCRs begins when G protein receptor kinases (GRKs) phosphorylate serine and threonine residues on the receptor's cytoplasmic tail and/or third intracellular loop (Pitcher et al., *Ann. Rev. Biochem.* 67:653 [1998]). The consequent binding of β-arrestin to phosphorylated GPCRs decreases their affinity for cognate heterotrimeric G proteins, thereby uncoupling the receptor from the G-βγ subunit by steric hindrance. In addition, dopamine D1 receptors can be phosphorylated and desensitized via a GRK3 mechanism (Tiberi et al., *J. Biol. Chem.* 271:3771 [1996]). Also, GRK3 expression is particularly high in doparninergic pathways in the central nervous system (Arriza et al., *J. Neurosci.* 12:4045 [1992]). While an understanding of the mechanism(s) is not necessary in order to use the present invention, these data are consistent with results observed during the development of the present invention that indicate GRK3 exerts an important regulatory effect on brain dopamine receptors. Because dopamine receptors play an important role in the action of amphetamine on the brain, it is believed that amphetamine-induced up-regulation of GRK3 counter-regulates dopamine receptor signalling initiated by mesocorticolimbic dopamine release. Indeed, this gene undergoes a dramatic up-regulation in rat frontal cortex in response to amphetamine challenge. However, it is not intended that the present invention be limited to any particular mechanism(s).

These data suggest that an apparent major physiological role for GRK3 in neurons is to act as a brake to limit excessive neural activity by inactivating G protein-coupled receptors. It is contemplated that defects in GRK3 function are associated with the inability to desensitize, resulting in a heightened responsiveness to dopamine signals in the brain. It is contemplated that in at least some cases, such genetic variation influences individual variation in behavioral sensitization to stimulants in humans and other animals. It is further contemplated that the present invention will provide means to predict whether individuals with mania have either low levels of the normal protein or high levels of mutated hypoactive protein. Conversely, it is contemplated that individuals with depression have either high levels of the normal protein or normal levels of mutated hyperactive protein. Indeed this predictive model is supported by post-mortem studies in people who had depression that led to suicide and who had increased levels of GRK2/3 protein in their PFC (Garcaia-Sevilla et al., *J. Neurochem.* 72:282 [1999]).

In order to test this hypothesis, levels of GRK3 protein in lymphoblastoid cell lines of individuals with bipolar disorder from families with evidence of linkage to 22q11 were tested (See, Example 5). Consistent with this model, three out of six such subjects demonstrated reduced expression of GRK3. These data suggest that a defect in transcriptional regulation in GRK3 contributes to the susceptibility to bipolar disorder in a subset of individuals. Thus, functional defects in this gene appear to prevent the normal desensitization to dopamine or other neurotransmitters, resulting in predisposition to psychiatric disorder(s).

During the development of the present invention, it was also determined that the defect in GRK3 appears to be a variation in sequences that regulate transcription of the gene. The gene was screened and no evidence of coding sequence defects was found. However, six sequence variants that may affect promoter function were identified (See, Example 3 and FIGS. 1 and 2). Thus, it is contemplated that the present invention will find use in screening and identifying drugs that augment GRK3 expression and/or function.

B. D Box Binding Protein (DBP)

D box binding protein (DBP) is a CLOCK-controlled transcriptional activator (Ripperger et al., *Genes Dev.* 14:679 [2000]), that shows a robust circadian rhythm. In mouse experiments (Yan et al., *J. Neurosci. Res.* 59:291 [2000]), its highest level of expression in the brain was found to be in the suprachaismatic nucleus (SCN), but it is also present in the cerebral cortex and caudate-putamen. In the SCN, DBP mRNA levels showed a peak at early daytime (ZT/CT4) and a trough at early nighttime in both light-dark and constant dark conditions. In the cerebral cortex and caudate-putamen, DBP mRNA was also expressed in a circadian manner, but the phase shift of DBP mRNA expression in these structures showed a 4-8 hour delay compared to the SCN. These data implicate DBP as an arm of the circadian clock. DBP knockout mice show reduced amplitude of the circadian modulation of sleep time, as well as a reduction in the consolidation of sleep episodes (Franken et al., *J. Neurosci.* 20:617 [2000]). Some clock genes have been shown to be essential for the development of behavioral sensitization to repeated stimulate exposure (Andretic et al., *Science* 285:1066 [1999]). Circadian rhythm abnormalities have also been implicated in mood disorders (See e.g., Kripke et al., *Biol. Psychiatr.* 13:335 [1978]; and Bunney and Bunney, *Neuropsychopharmacol.* 22:335 [2000]).

DBP maps to chromosome 19q13.3. Chromosome 19 has not been a strong linkage region for psychiatric disorders, although one study has implicated this region in a large Canadian kindred with bipolar disorder (Morissette et al., *Am. J. Med. Genet.* 88:567 [1999]). In this sample, D19S867, which is approximately 2 cM from DBP yielded a lod score of 2.6. Taken together, the connections between clock genes, stimulant sensitization and circadian rhythmicity suggest a potential role for DBP in mood disorders.

C. Farnesyl-diphosphate Farnesyltransferase 1 (FDFT1)

FDFT1, also known as "human squalene synthase" (HSS), is involved in the first step of sterol biosynthesis uniquely committed to the synthesis of cholesterol (Schechter et al., *Genomics* 20:116 [1994]). As such, it has received attention as a target for the development of cholesterol-lowering drugs. Interestingly, primary prevention human trials have shown a correlation between lowering cholesterol and suicide, postulated to occur due to lowering the numbers of serotonin receptors in synapses (Engelberg, *Lancet* 339:727 [1992]). Studies in monkeys have also shown an association between cholesterol and central serotonergic activity (Kaplan et al., *Ann. NY Acad. Sci.* 836:57 [1997]). Mice homozygously disrupted for the squalene synthase gene exhibited embryonic lethality and defective neural tube closure, implicating de novo cholesterol synthesis in nervous system development (Tozawa et al., *J. Biol. Chem.* 274:30843 [1999]). Moreover, de novo cholesterol synthesis was shown to be important for neuronal survival., and apoE4, which is a major risk factor for Alzheimer's disease, has been implicated in inducing neuronal cell death through the suppression of de novo cholesterol synthesis (Michikawa and Yanagisawa, *Mech. Ageing Dev.* 107:223 [1999]). As such, it is contemplated that neuronal cholesterol synthesis, of which squalene synthase is a key regulator, is positively correlated with both elevated mood and neuronal survival. Nonetheless, an understanding of the mechanism(s) is not necessary in order to use the present invention, nor is it intended that the present invention be limited to any particular mechanism(s).

FDFT1 is located on 8p23.1-p22, near the telomere. Numerous studies have implicated 8p in both schizophrenia and bipolar disorder. However, most of these results are about 40-50 cM centromeric to FDFT1. Two studies have reported evidence for linkage to schizophrenia within 10 cM of FDFT1. Wetterberg et al. (Wetterberg et al., *Am. J. Med. Genet.* 81:470 [Abstract] [1998]), reported a lod score of 3.8 at D8S264, in a large Swedish isolate. The NIMH Schizophrenia Genetics Consortium also reported evidence implicating a broad area of 8p in African American pedigrees, including two putative peaks, with one at D8S264 (NPL Z score 2.3) (Kaufmann et al., *Am. J. Med. Genet.* 81:282 [1998]).

D. Vertebrate LIN7 Homolog 1 (MALS-1 or VELI1)

MALS-1 is a PDZ domain-containing cytoplasmic protein that is enriched in brain synapses where it associates in complexes with PSD-95 and NMDA type glutamate receptors (Jo et al., *J. Neurosci.* 19:4189 [1999]). It has been implicated in regulation of neurotransmitter receptor recruitment to the post-synaptic density, as well as being part of a complex with CASK and Mint 1 that couples synaptic vesicle exocytosis to cell adhesion (Butz et al., *Cell* 94:773 [1998]).

MALS-1 maps to 12q21.3, in a region implicated in several studies of bipolar disorder. This region was first reported in bipolar disorder through observation of a Welsh family in which bipolar disorder and Darier's disease co-segregated (Dawson et al., *Am. J. Med. Genet.* 60:94 [1995]). Though the Darier's region is somewhat distal to MALS-1, Morisette et al. reported evidence of linkage of bipolar disorder to markers on 12q, with a maximum at D12S82 ($Z_{all}$ 4.0, lod score 2.2), which is approximately 2 cM from MALS-1 (Morisette et al., supra).

E. Sulfotransferase 1 A1 (SULT1A1)

SULT1A1 is a sulfotransferase that inactivates dopamine and other phenol-containing compounds by sulfation. It is contemplated as playing a role in limiting the neuronal stimulatory and psychosis promoting effects of dopamine. Though it is not a primary regulator of synaptic dopamine concentration, a defect in this gene could lead to impaired clearing of dopamine from the extracellular space with a resulting amphetamine-like effect. SULT1A1 has not yet been precisely mapped, but cytogenetic data locate it to chromosome 16p12.1-p11.2, near a genomic locus implicated in bipolar disorder (D16S510, lod score 2.5) (Ewald et al., *Psychiatr. Genet.* 5:71 [1995]), and alcohol dependence (D16S675, lod score 4.0)(Foroud et al., *Alcohol Clin. Exp. Res.* 22:2035 [1998]).

F. Insulin-Like Growth Factor 1 (IGF1)

IGF1 stimulates increased expression of tyrosine hydroxylase, the rate limiting enzyme in the biosynthesis of dopamine (Hwang and Choi, *J. Neurochem.* 65:1988 [1995]). It has also been shown to have trophic effects on doparnine brain neurons and to protect doparnine neurons from apoptotic death (Knusel et al., *Adv. Exp. Med. Biol.* 293:351 [1991]). IGF1 also induces phosphatidylinositol 3-kinase survival pathways through activation of AKT1 and AKT2; it is inhibited by TNF in its neuroprotective role. IGF1 gene disruption in mice results in reduced brain size, CNS hypomyelination, and loss of hippocampal granule and striatal parvalbumin-containing neurons (Beck et al., *Neuron* 14:717 [1995]). Defects of IGF1 in humans produce growth retardation with deafness and mental retardation. IGF1 is located on chromosome 12q22-q24.1. It is at a map position of 109 cM, 13 cM telomeric to MALS-1, and is in the same 40 cM region described above. This region is implicated in bipolar disorder and extends from D12S82 at 96 cM (NPL $Z_{all}$ 4.0) (Morisette et al., supra) to PLA2 at 136 cM (lod score 2.49) (Dawson et al., supra).

G. Additional Genes

Two additional genes met the criteria of reproducibility and mapping to a linkage region, but their functions identified to date make them less likely to be disease gene candidates. RNA polymerase II polypeptide (POLR2F) maps to 22q13.1, approximately 10 cM distal to D22S278, which has been implicated in several studies of both bipolar disorder and schizophrenia, as described above. POLR2F is responsible for mRNA production and may control cell size (Schmidt and Schibler, *J. Cell Biol.* 128:467 [1995]), and overall body morphological features (Bina et al., *Prog. Nucl. Acid Res. Mol. Biol.* 64:171 [2000]). It is more active in metabolically active cells (Schmidt and Schibler, supra). FCGRT is a receptor for the Fc component of IgG. It structurally resembles the major histocompatibility class I molecule (Kandil et al., *Cytogenet. Cell Genet.* 73:97 [1996]). FCGRT maps to 19q13.3, near DBP and a marker implicated in bipolar disorder, as discussed above. It is contemplated that activation of these genes is a secondary effect of amphetamine and their mapping near linkage regions is coincidental.

Several other genes did not meet the stringent criteria used in the development of the present invention. For example, fibroblast growth factor receptor 1 (FGFR1) had an average fold change of 4.1, though the increase was only 1.8 fold in one of the two experiments. Increased expression of astrocytic basic FGF in response to amphetamine was previously demonstrated (Flores et al., *J. Neurosci.* 18:9547 [1998]). Furthermore, FGF-2, a ligand for FGFR1 has been shown to regulate expression of tyrosine hydroxylase, a critical enzyme in dopamine biosynthesis (Rabinovsky et al., *J. Neurochem.* 64:2404 [1995]). FGFR1 maps to chromosome 8p11.2-p11.1, approximately 10 cM centromeric to a genomic locus near D8D1771 (8p22-24), which demonstrated evidence of linkage to schizophrenia in several studies (See e.g. Blouin et al., *Nat. Genet.* 20:70 [1998]; Kendler et al., *Am. J Psychiatr.* 153:1534 [1996]; and Levinson et al., *Am. J. Psychiatr.* 155:741 [1998]). Heat shock 27 kD protein 1 (HSP27, HSPB1) has been implicated in stress resistance responses in a variety of tissues. It is hypothesized that it plays a role in promoting neuronal survival (See e.g. Lewis et al., *J. Neurosci.* 19:8945 [1999]), and may be induced in the brain by kainic acid-induced seizure (Kato et al., *J. Neurochem.* 73:229 [1999]). HSPB1 maps to 7q22.1, approximately 20 cM from a region implicated in bipolar disorder in two independent samples (Detera-Wadleigh et al., *Am. J. Med. Genet.* 74:254 [1997]; and Detera-Wadleigh et al., *Proc. Natl. Acad. Sci. USA* 96:5604 [1999]).

In view of the number of genomic regions that have been implicated in bipolar disorder and schizophrenia, it was considered to be important to evaluate the probability that some of the genes identified during the development of the present invention mapped to a disease locus by chance. As indicated above, it was required that a gene map to within 10 cM of a marker identified in at least one study, as having suggestive evidence of linkage. Assuming that the average genomic region meeting the criteria used in the present invention is 30 cM long, and approximately 20 such regions have been reported, then about 20 percent of the genome is implicated in bipolar disorder or schizophrenia. Therefore, there is about a 20 percent probability that a gene will fall within a putative linkage region by chance. However, the animal model gene expression methods of the present invention identified about 1 in 1000 genes as being changed. Assuming that there are 75,000 genes in the genome, then each 30 cM linkage region would contain on average, 750 genes, and the approach of the present invention would identify approximately 1 gene. Thus, there is an estimated probability of 1 in 5,000 that a gene would meet both criteria by chance. Clearly, not all genes identified by this approach are genes for these disorders. Nonetheless, the present invention provides methods that are useful in the diagnosis and treatment of psychiatric disorders.

Using methods presently known in the art, definitive identification of disease genes typically requires the discovery of a polymorphism of functional significance and its association with illness. In addition, large-scale sequencing of both coding and non-coding regions in numerous affected individuals is needed. Assuming that there is an average of 750 genes per linkage region, this represents an enormous task. In contrast, the convergent functional genomics approach of the present invention provides a relevant animal model, methods and compositions to identify a small number of candidates for exhaustive mutation screening. Thus, the present invention provides methods that effectively reduce the scale of such a project by several hundred fold.

It is further contemplated that the high-probability candidate genes for mania and psychosis identified using the convergence of animal model data and human genetic linkage data will be studied in detail for genomic variation in clinical populations and behavioral variation in knockout animal models. In addition, it is contemplated that the convergent functional genomics methods of the present invention will find use with various other polygenic diseases. Indeed, it is not intended that the present invention be limited to psychiatric diseases nor any other particular disease syndrome.

II. Psychogenes and Psychosis-Suppressor Genes

The present invention provides evidence that genes involved in psychiatric disorders can be placed into two prototypical categories. Genes whose activity promotes processes that lead to mania or psychosis are referred to herein as "psychogenes" (i.e., analogous to oncogenes). Conversely, genes whose activity suppresses processes that lead to these psychiatric disorders are referred to herein as "psychosis-suppressor" genes (i.e., analogous to tumor suppressor genes). Thus, based on the results observed during the development of the present invention, DBP, FGFR1, NTRK3, FDFT1, MALS-1, IGF1 are psychogenes, while GRK3, SULT1A1, and ADORA3 are psychosis-suppressor genes. However, it is not intended that the present invention be limited to these particular genes. Indeed, it is contemplated that additional genes and variants will be identified using the methods and compositions of the present invention. Although this classification is simplistic, it has heuristic value for psychiatric illness. It is contemplated that this classification will find use in considerations regarding the role(s) of these putative disease genes in pathophysiology and as targets for therapeutic intervention.

In particularly preferred embodiments, the present invention finds use in the identification and characterization of dysfunctions in these genes. In some embodiments, the DNA of patients with psychiatric disorders (e.g., bipolar disorder, schizophrenia, etc.) is screened in order to detect DNA sequence variants that are associated with or lead to dysfunction of these genes. In other embodiments, DNA of patients suspected of suffering from psychiatric disorders, as well as DNA of normal subjects who wish to be screened for psychiatric disorders, is tested to screen for the presence of these genetic variants and predict risk for psychiatric illness later in life. In some embodiments, these methods find use in clarifying and/or confirming diagnosis of psychiatric disorders.

In addition to the diagnostic value of these methods, the present invention also provides means to determine the prognosis of affected patients, as well as predict treatment outcomes. For example, in some embodiments, patients with psychiatric illness who have been treated with medication are tested for these genetic variants, in order to determine the treatment efficacy, as well as to gather evidence as to the medications that are useful in treatment of patients suffering from particular psychiatric disorders. In other embodiments, cells from these patients may be used to assess the treatment efficacy of one or more drugs. In some embodiments, screening tests based on binding and/or functional blockade of dopamine receptors, the dopamine transporter, other neurotransmitter receptors, and/or transporters are used to identify useful compounds in cell culture and/or animal models (e.g., the rat model described in Example 1). In some embodiments, test compounds are compared with compounds known to block dopamine receptors, the dopamine transporter, and/or other neurotransmitter receptors or transporters. In still further embodiments, it is contemplated that simple tests will find use in monitoring the ongoing response of patients to treatment. For example, it is contemplated that a blood test for GRK3 expression will find use in monitoring the efficacy of patient therapy. However, it is not intended that the present invention be limited to GRK3 expression, as any suitable protein finds use in the present invention.

It is contemplated that the present invention will also find use in screening and identifying drugs that interact with a dysfunctional protein to enhance its function. In some embodiments, the present invention provides methods and compositions to screen drugs that interact with the gene itself or proteins that bind regulatory sequences in the gene and thereby enhance transcription. Thus, it is contemplated that any of several upstream targets will be identified using the present invention, based on their role(s) in regulating the expression of gene(s) of interest. It is further contemplated that such upstream targets will provide superior points of drug intervention and find use in drug design. Indeed, the in vivo and in vitro methods of the present invention provide the means to monitor the expression and/or function of upstream targets based on their ability to indirectly modify the function of the dysfunctional gene or protein. Similarly, proteins downstream of the dysfunctional protein that are involved in the functional pathway of the dysfunctional gene/protein also find use, as well as proteins that interact with and/or facilitate the overall function of the dysfunctional gene. Thus, the present invention provides methods and compositions for the upstream and downstream assessment of test compounds in functional assay systems.

In addition to the diagnostic, prognostic and drug assessment advances provided by the present invention, the present invention also provides methods and compositions suitable for use in gene therapy regimens. In gene therapy embodiments, treatments that find use increase the expression and/or function of psychosis-suppressor genes and/or decrease the expression and/or function of psychogenes. For example, it is contemplated that GRK3 represents an ideal target for gene therapy methods. The genetic defect appears to be a hypomorph that manifests phenotypically as a recessive trait. Thus, it is contemplated that gene therapy methods that increase or normalize expression of GRK3 in relevant brain regions will find use in treatment of psychiatric disorders (e.g., bipolar disorder, schizophrenia, etc.). However, it is not intended that the present invention be limited to GRK3 protein, as any suitable protein finds use in these methods.

It is also contemplated that the present invention will find use in protein-based therapies. In these regimens, the protein is delivered directly to the cells deficient in the function of a particular gene/protein. Thus, it is contemplated that any suitable method for the delivery of proteins for therapeutic purposes will find use in the present invention, including but not limited to such methods as the use of fusion proteins (e.g., fusion proteins that include a "passport" domain which facilitates transport of proteins across cell membranes). For example, it is contemplated that normal GRK3 protein will be delivered to neurons using one or more of these methods. However, it is not intended that the present invention be limited to GRK3 protein, as any suitable protein finds use in these methods.

III. Cell Culture Methods

In addition to the convergent functional genomics methods described above in which in vivo experimental results are used in conjunction with genome mapping data, the present invention also provides cell culture methods to detect and characterize psychogenes and psychosis-suppressor genes (described in greater detail below). In addition, these methods find use in the screening and detection of compounds that change the function of these genes. For example, it is contemplated that these cell culture methods will find use in detection of compounds that increase the action of psychosis suppressor genes in either or both the basal and agonist-challenged states.

In some embodiments, lymphoblastoid cell lines (e.g., similar to those described in Example 3) are exposed to various compounds. In particularly preferred embodiments, cells from normal control subjects, and cells from subjects with at least one psychiatric disorder (e.g., bipolar disorder) are tested and compared. In some embodiments, the cells are tested under conditions in which the cells are exposed to the test compound alone, as well as under conditions in which the cells are also challenged with a dopamine agonist. In particularly preferred embodiments, cells from subjects with bipolar disorder who are shown to have defects in the genes described above are used. In these analyses, testing parameters include mRNA expression of the gene of interest, protein expression, and/or functional measures specific for each gene of interest. In yet other particularly preferred embodiments, compounds of interest increase the expression and function of psychosis-suppressor genes and/or decrease the expression and function of psychogenes in the basal state and preferably in the presence of the dopamine agonist.

Definitions

As used herein, the term "mood" refers to an individual's enduring emotional state, while "affect" refers to short-term fluctuations in emotional state. Thus, the term "mood disorder" is used in reference to conditions in which abnormalities of emotional state are the core symptoms. The most common serious mood disorders reportedly seen in general medical practice are major depression (unipolar depression), dysthymic disorder (chronic, milder form of depression), and bipolar disorder (manic-depressive illness).

As used herein, the term "psychiatric disorder" refers to mental, emotional, or behavioral abnormalities. These include but are not limited to bipolar disorder, schizophrenia, schizoaffective disorder, psychosis, depression, stimulant abuse, alcoholism, panic disorder, generalized anxiety disorder, attention deficit disorder, post-traumatic stress disorder, and Parkinson's disease.

The term "bipolar disorder," as used herein, refers to any of several mood disorders characterized usually by alternating episodes of depression and mania (e.g., bipolar disorder I) or by episodes of depression alternating with mild nonpsychotic excitement or hypomania (e.g., bipolar disorder II). Individual's at risk of developing bipolar disorder include those with a family history of bipolar disorder. Those at greatest risk have first degree relatives which are diagnosed with bipolar disorder I or II.

The terms "gene associated with a psychiatric disorder" and "psychiatric gene," as used herein, refer to genes whose activity plays a role in the processes leading to development of psychiatric disorders. This role may be one of promotion or suppression and thus encompasses both psychogenes and psychosis-suppressor genes.

The terms "marker associated with" and genetic linkage refer to the greater association in inheritance of two or more nonallelic genes than would be expected from independent assortment (e.g., genes are linked because they reside near each other on the same chromosome).

As used herein, the term "psychogenes" refers to genes whose activity promotes processes that lead to mania or psychosis (i.e., analogous to oncogenes). Conversely, genes whose activity suppresses processes that lead to mania or psychosis are referred to herein as "psychosis suppressor genes" (i.e., analogous to tumor suppressor genes).

The terms "microarray," "GeneChip," "genome chip," and "biochip," as used herein, refers to an ordered arrangement of hybridizeable array elements. The array elements are arranged so that there are preferably at least one or more different array elements on a substrate surface. The hybridization signal from each of the array elements is individually distinguishable. In a preferred embodiment, the array elements comprise oligonucleotides, although the present invention could also be used with cDNA or other types of nucleic acid array elements.

As used herein, the term "altered expression" refers to differences in gene expression observed upon comparing cells incubated under test and control conditions. This term encompasses both induced (e.g., increased expression) genes and repressed (e.g., decreased expression) genes. In preferred embodiments the fold change in expression between test and control conditions is greater than two in at least two experiments.

The term "hybridization score," as used herein refers to the degree of binding observed between a probe and a nucleic acid array element of the microarray or GeneChip. In some embodiments, this score is determined by measuring the fluorescence intensity of a labelled probe, although this invention is not limited to the use of fluorescent quantification techniques.

As used herein, the term "labelled" refers to the attachment of a traceable constituent to a biological molecule in order to more easily quantify or trace the biological molecule of interest. In some embodiments, the label may be a fluorescent, luminescent, enzymatic or radioactive label. For instance, probe hybridization to a nucleic acid array element may be measured by directly or indirectly (e.g. via a biotin/avidin or a biotin/streptavidin linkage) attaching a phycoerythrin or fluorescein tag to the probe.

As used herein, the term "sequence variation" refers to differences observed in nucleic acid sequence between individuals. "Sequence variation" includes both "single nucleotide polymorphisms," as well as larger stretches of differences.

The term "single nucleotide polymorphism" (SNP), refers to single differences observed in a given position of a nucleic acid sequence between individuals. These polymorphisms may be the result of point mutations and include substitutions such as transitions and transversions. "Transitions" are a change of a pyrimidine nucleotide, C or T, into an other pyrimidine nucleotide, or a change of a purine nucleotide, A or G, into an other purine nucleotide. "Transversions" are a change of a pyrimidine nucleotide, C or T, into a purine nucleotide, A or G, or vice versa Transitions are more common than transversions. As used herein, the term SNP also includes single nucleotide deletions and insertions.

As used herein, the term "human homologue" refers to a human gene which shares a common ancestor with a gene from another species. Homologous genes can be identified as such by determining the percent identity of two nucleic acid sequences or can be inferred by comparing the predicted structure of the proteins encoded by these genes.

A "variant" of a protein of interest, as used herein, refers to an amino acid sequence that is altered by one or more amino acids. The variant may have "conservative" changes, wherein a substituted amino acid has similar structural or chemical properties, (e.g., replacement of leucine with isoleucine). More rarely, a variant may have "nonconservative" changes (e.g., replacement of a glycine with a tryptophan). Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

As used herein, the terms "translation start site" and "start codon" refer to the ATG or AUG encoding the first amino acid moiety (e.g., methionine) of a nascent polypeptide chain. This may not be the first ATG or AUG codon found in the message and the methionine encoded by this triplet may not be present in the processed, mature form of the polypeptide or protein.

The term "biologically active," as used herein, refers to a protein or other biologically active molecule (e.g., catalytic RNA) having structural., regulatory, or biochemical functions of a naturally occurring molecule. Likewise, "immunologically active" refers to the capability of the natural, recombinant, or synthetic protein or any oligopeptide or polynucleotide thereof, to induce a specific immune response in appropriate animals or cells and to bind with specific antibodies.

As used herein, the term "dopamine agonist" refers to any compound which has activities similar to that of dopamine by virtue of binding to dopamine receptors. The dopamine agonists of the present invention include but are not limited to amphetamine, methamphetamine, cocaine and methylphenidate.

The term "agonist," as used herein, refers to a molecule which, when bound to a compound of interest, causes a change in the compound, which modulates the activity of the compound. Agonists may include proteins, nucleic acids, carbohydrates, or any other molecules which bind or interact with the compound.

The terms "antagonist" and "inhibitor," as used herein, refer to a molecule which, when bound to a compound of interest, blocks or modulates the biological or immunological activity of the compound of interest. Antagonists and inhibitors may include proteins, nucleic acids, carbohydrates, or any other molecules which bind or interact with the compound of interest.

The term "modulate," as used herein, refers to a change or an alteration in the biological activity of a compound of interest. Modulation may be an increase or a decrease in protein activity, a change in binding characteristics, or any other change in the biological functional, or immunological properties of the compound of interest.

The term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence which encodes a gene product. The coding region may be present in either a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al., *Science* 236:1237 [1987]). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (Voss et al., *Trends Biochem. Sci.* 11:287 [1986]; and Maniatis et al., supra). For example, the SV40 early gene enhancer is very active in a wide variety of cell types from many mammalian species and has been widely used for the expression of proteins in mammalian cells (Dijkema et al., *EMBO J.* 4:761 [1985]). Two other examples of promoter/enhancer elements active in a broad range of mammalian cell types are those from the human elongation factor 1α gene (Uetsuki et al., *J. Biol. Chem.* 264:5791 [1989]; Kim et al., *Gene* 91:217 [1990]; and Mizushima and Nagata, *Nuc. Acids. Res.* 18:5322 [1990]) and the long terminal repeats of the Rous sarcoma virus (Gorman et al., *Proc. Natl. Acad. Sci. USA* 79:6777 [1982]) and the human cytomegalovirus (Boshart et al., *Cell* 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site (Sambrook et al., *Molecular Cloning: A Laboratory Manual,* 2nd ed., Cold Spring Harbor Laboratory Press, New York [1989], pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6-16.7).

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence or probe to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30 percent identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

A gene may produce multiple RNA species which are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands.

The equation for calculating the $T_m$ of nucleic acids is well known in the art. As indicated by standard references, a simple estimate of the $T_m$ value may be calculated by the equation: $T_m=81.5+0.41$ (percent G+C), when a nucleic acid is in aqueous solution at 1 M NaCl (See e.g., Anderson and Young, Quantitative Filter Hybridization, in *Nucleic Acid Hybridization* [1985]). Other references include more sophisticated computations which take both structural and sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acids.

Template specificity is achieved in most amplification techniques by the choice of enzyme. Amplification enzymes are enzymes that, under the conditions they are used, will process only specific sequences of nucleic acid in a heterogeneous mixture of nucleic acids. For example, in the case of Qβ replicase, MDV-1 RNA is the specific template for the replicase (Kacian et al., *Proc. Natl. Acad. Sci. USA* 69:3038 [1972]). Other nucleic acids will not be replicated by this amplification enzyme. Similarly, in the case of T7 RNA polymerase, this amplification enzyme has a stringent specificity for its own promoters (Chamberlin et al., *Nature* 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, *Genomics* 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (Erlich (ed.), *PCR Technology*, Stockton Press [1989]).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label. The present invention provides sequences for suitable for use as probes.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of Mullis (See e.g., U.S. Pat. Nos. 4,683,195 4,683,202, and 4,965,188, herein incorporated by reference), which describes a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labelled probe; incorporation of biotinylated primers followed by avidin-enzyme conjugate detection; incorporation of $^{32}$P-labelled deoxynucleotide triphosphates, such as dCTP or DATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "antisense" is used in reference to RNA sequences which are complementary to a specific cDNA or RNA sequence (e.g., mRNA). Included within this definition are antisense complementary RNA (cRNA) molecules produced by an in vitro transcription method from a CDNA template. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein, the term "polyA$^+$ RNA" refers to RNA molecules having a stretch of adenine nucleotides at the 3' end. This polyadenine stretch is also referred to as a "poly-A tail." Eukaryotic mRNA molecules contain poly-A tails and are referred to as polyA$^+$ RNA.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acids encoding a protein includes, by way of example, such nucleic acids in cells ordinarily expressing the protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA which is produced by transcription of genes located on a chromosome (e.g., hnRNA and mRNA) and cDNA copies of the RNA transcribed from the DNA located on a chromosome. Sequences associated with a chromosome may be detected by numerous techniques including probing of Southern and Northern blots and iii situ hybridization to RNA, DNA or metaphase chromosomes with probes containing sequences homologous to the nucleic acids in the above listed preparations.

As used herein the term "coding region" when used in reference to structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast "regulatory genes" are structural genes which encode products which control the expression of other genes (e.g., transcription factors).

As used herein, the term "purified" or "to purify" refers to the removal of contaminants from a sample. For example, antibodies are purified by removal of contaminating non-immunoglobulin proteins; they are also purified by the removal of immunoglobulin that does not bind the antigen of interest. The removal of non-immunoglobulin proteins and/or the removal of immunoglobulins that do not bind the antigen of interest results in an increase in the percent of immunoglobulins in the sample that bind the antigen of interest. In another example, recombinant polypeptides are expressed in bacterial host cells and the polypeptides are purified by the removal of host cell proteins; the percent of recombinant polypeptides is thereby increased in the sample.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "fusion protein" refers to a chimeric protein containing the protein of interest (or fragments thereof) joined to an exogenous protein fragment. The fusion partner may enhance solubility of the protein of interest as expressed in a host cell, may provide an affinity tag to allow purification of the recombinant fusion protein from the host cell or culture supernatant, or both. If desired, the fusion protein may be removed from the protein of interest by a variety of enzymatic or chemical means known to the art.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labelled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labelled probe to detect RNA species complementary to the probe used. Northern blots are a standard tool of molecular biologists (Sambrook et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (i.e., an epitope). When a protein or fragment of a protein is used to immunize a host animal., numerous regions of the protein may induce the production of antibodies which bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The terms "specific binding" and specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labelled "A" and the antibody will reduce the amount of labelled A bound to the antibody.

The present invention also contemplates "non-human animals" comprising any non-human animal capable of overexpressing mRNA and/or proteins of interest. Such non-human animals include vertebrates such as rodents, non-human primates, ovines, bovines, ruminants, lagomorphs, porcines, caprines, equines, canines, felines, aves, etc. Preferred non-human animals are selected from the order Rodentia, most preferably mice. The term "order Rodentia" refers to rodents (i.e., placental mammals [Class Euthria] which include the family Muridae (rats and mice).

The "non-human animals having a genetically engineered genotype" of the invention are preferably produced by experimental manipulation of the genome of the germline of the non-human animal. These genetically engineered non-human animals may be produced by several methods including the introduction of a "transgene" comprising nucleic acid (usually DNA) into an embryonal target cell or integration into a chromosome of the somatic and/or germ line cells of a non-human animal by way of human intervention, such as by the methods described herein. Non-human animals which contain a transgene are referred to as "transgenic non-human animals." A transgenic animal is an animal whose genome has been altered by the introduction of a transgene.

The term "transgene" as used herein refers to a foreign gene that is placed into an organism by introducing the foreign gene into newly fertilized eggs or early embryos. The term "foreign gene" refers to any nucleic acid (e.g., gene sequence) which is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the protein of interest mRNA-specific signal observed on Northern blots). The amount of mRNA present in the band corresponding in size to the correctly spliced protein transgene RNA is quantified; other minor species of RNA which hybridize to the transgene probe are not considered in the quantification of the expression of the transgenic mRNA The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

As used herein, the term "selectable marker" refers to the use of a gene which encodes an enzymatic activity that confers the ability to grow in medium lacking what would otherwise be an essential nutrient (e.g., the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity which can be detected in any eukaryotic cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene which is used in conjunction with tk$^-$ cell lines, the CAD gene which is used in conjunction with CAD-deficient cells and the mammalian hypoxanthine-guanine phosphoribosyl transferase (hprt) gene which is used in conjunction with hprt$^-$ cell lines. A review of the use of selectable markers in mammalian cell lines is provided in Sambrook et al., *Molecular Cloning: A Laboratory Manual*, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

The terms "compound" and "test compound" refer to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of cancer.

A "composition comprising a given polynucleotide sequence" as used herein refers broadly to any composition containing the given polynucleotide sequence. The composition may comprise an aqueous solution.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

Experimental

The following examples are provided in order to demonstrate and further illustrate certain preferred embodiments and aspects of the present invention and are not to be construed as limiting the scope thereof.

In the experimental disclosure which follows, the following scientific abbreviations/notations apply: lod (log of odds); PFC (prefontal cortex); amygdala (AMY); SNP (single nucleotide polymorphism); ° C. (degrees Centigrade); rpm (revolutions per minute); BSA (bovine serum albumin); CFA (complete Freund's adjuvant); IFA (incomplete Freund's adjuvant); IgG (immunoglobulin G); IM (intramuscular); IP (intraperitoneal); IV (intravenous or intravascular); SC (subcutaneous); $H_2O$ (water); HCl (hydrochloric acid); aa (amino acid); bp (base pair); kb (kilobase pair); kD (kilodaltons); cM (centimorgans); gm or g (grams); μg (micrograms); mg (milligrams); ng (nanograms); μl (microliters); ml (milliliters); mm (millimeters); nm (nanometers); μm (micrometer); M (molar); mM (millimolar); μM (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{600}$ (optical density at 600 nm); PAGE (polyacrylamide gel electrophoresis); PBS (phosphate buffered saline [150 mM NaCl, 10 mM sodium phosphate buffer, pH 7.2]); PCR (polymerase chain reaction); PEG (polyethylene glycol); PMSF (phenylmethylsulfonyl fluoride); SDS (sodium dodecyl sulfate); w/v (weight to volume); v/v (volume to volume);

As used herein, the following abbreviations also apply: ABI (Applied Biosystems, Fosterter City, Calif.); Affymetrix (Affymetrix, Santa Clara, Calif.); Santa Cruz (Santa Cruz Biologicals, Santa Cruz, Calif.); Amersham (Amersham Pharmacia Biotech, Piscataway, N.J.); Amicon (Amicon, Inc., Beverly, Mass.); ATCC (American Type Culture Collection, Rockville, Md.); BioRad (BioRad, Richmond, Calif.); Clontech (CLONTECH Laboratories, Palo Alto, Calif.); GIBCO BRL or Gibco BRL (Life Technologies, Inc., Gaithersburg, Md.); Hewlett-Packard (Hewlett-Packard Company, Palo Alto, Calif.); Invitrogen (Invitrogen-Novex, San Diego, Calif.); Molecular Dynamics (Molecular Dynamics, Sunnyvale, Calif.); New England Biolabs (New England Biolabs, Inc., Beverly, Mass.); Novagen (Novagen, Inc., Madison, Wis.); Perlin Elmer (PE Biosystems, Foster City, Calif.); Promega (Promega Corp, Madison, Wis.); Sigma (Sigma Chemical Co., St. Louis, Mo.); Stratagene (Stratagene Cloning Systems, La Jolla, Calif.); Sun (Sun Microsystems Inc., Palo Alto, Calif.); and Weizmann Institute (Weizmann Institute of Science, Rehovot, Israel).

EXAMPLE 1

Amphetamine Treatment

In these experiments, a rat animal model was used to identify susceptibility genes. These experiments were done twice, independently, with different sets of animals and at different times, to assess reproducibility.

Three Sprague Dawley rats were treated with 4 mg/kg amphetamine, while another three rats were treated with normal saline injection (i.e., negative-control animals). After 24 hours, the rats were humanely sacrificed and the brains were harvested.

EXAMPLE 2

Tissue Testing and Analysis

In these experiments, the brain tissues obtained from the rats described in Example 1 were processed and tested. Samples were handled according to the recommendation of Affymetrix, the manufacturer of the GeneChips used during the development present invention In the experiments described in greater detail below, the Affymetrix U34A chip, which measures 7,000 cDNAs and 1,000 ESTs, was used. The analyses were conducted at the University of California, San Diego/Veteran's Administration Center GeneChip Core Facility.

Tissues from each brain region from the three animals in each experimental group were pooled (i.e., test and control animals). Total RNA was isolated from the tissue using standard protocols known in the art. Briefly, STAT-60 extraction buffer, and phenol/chloroform extraction was used. cDNA was synthesized and used as templates to produce biotin-labelled antisense cRNAs using an in vitro transcription reaction. After fragmentation, the CRNA hybridization cocktail was prepared, cleaned, and applied to the Affymetrix GeneChip oligonucleotide array. The loaded GeneChip was incubated overnight in a GeneChip hybridization oven. Immediately following hybridization, the probe array was washed and then stained with a streptavidin-phycoerythrin (SAPE) fluorescence tag. The GeneChip Fluidics Station was used to automate the washing steps to remove non-specifically bound cRNA and stain.

Once the probe array was hybridized, stained and washed, it was scanned using an Hewlett-Packard GeneArray scanner. The GeneChip Operating System, running on a PC workstation, controlled the scanner functions and collected fluorescence intensity data. Data were processed using GeneChip expression analysis software from Affymetrix. A two-fold increase or decrease in expression was chosen as a conventional empirical cut-off. Thus, at least a two-fold change in each of two independent animal experiments was used to select those genes with the most robust and reproducible change in expression. In these analyses, standard default settings of the Affymetrix GeneChip Expression Algorithm were used. A gene had to be called "Present" and "Changed," in at least one out of two experiments and had to have an Average Difference Change greater than 50, as well as a fold change greater than 2 in two out of two experiments. Genes meeting this criteria are summarized in Table 1, for the prefrontal cortex (PFC) and Table 2, for the amygdala (AMY). The genes that were induced more than two-fold in both experiments were also identified by their GenBank accession numbers, as indicated in the Tables. A gene was scored as mapping to a linkage region for either schizophrenia (S) or bipolar disorder (B) if its human homologue mapped to within 10 cM of a marker for which at least suggestive evidence of linkage had been reported.

The chromosomal locations of the human homologues of these genes were then compared with published linkage reports for bipolar disorder and schizophrenia, as well as data generated during the development of the present invention to cross-validate the results and identify high-probability candidate genes. The human homologues and human chromosomal map locations were determined using the NCBI database. GeneCard (Weizmann Institute), a comprehensive database containing all of the various information available regarding known genes and their functions was also used for each gene identified in the screen. Genes were considered to be positional candidates (i.e., close to a genomic hotspot) if they mapped to within 10 cM of a marker for which there was at least one report of suggestive evidence of linkage (Lander and Kruglyak, *Nat. Genet.*, 11:241 [1995]). The Marshfield integrated linkage map was used as a reference for genetic location. As shown in Tables 1 and 2, eight of these genes met the criteria used in the analyses described in the Examples herein. It was also noted that a number of interesting genes were very narrowly positioned below this threshold. An indication of the specificity of the result is that GRK2, a close homologue of GRK3, demonstrated no change in expression in either experiment (fold changes of 1.1 and 1.0 in two experiments).

EXAMPLE 3

Mutation Screening of GRK3

In these experiments, portions of the GRK3 gene locus were amplified and directly sequenced from 14 bipolar patients and 6 control subjects.

The GRK3 gene spans 21 exons over 170 kb. Using the available genomic sequence, PCR primers were designed so as to individually amplify each of the 21 exons including approximately 200 bp of flanking intronic sequence which contains splicing signals. Primers were also designed to amplify approximately 1.6 kb in the 5' promoter region in four overlapping segments. In order to enrich the sample to be screened for those subjects most likely to contain a functional mutation in the GRK3 gene, families were identified from the 20 families that were part of an earlier genome scan and the 57 NIMH families which showed a positive lod score for the marker D22S419. Fourteen such bipolar subjects were identified and their DNA was PCR amplified for each of these regions. In addition to these 14 affected subjects from families with evidence of linkage, another set of 6 control subjects were screened in order to identify high frequency anonymous sequence variants in introns suitable as markers for linkage disequilibrium studies. These double stranded PCR fragments were then sequenced directly using cycle sequencing and fluorescent detection. Sequencing reactions were electrophoretically separated and detected using an ABI 377 automated DNA sequencer. The resulting electropherograms were analyzed for single nucleotide polymorphisms (SNPs) as both homozygotes and heterozygotes using the software package PolyPhred (Nickerson et al., *Nucleic Acids Res* 25:2745-2751 [1997]).

The results of these experiments are summarized in FIGS. 1 and 2. No coding sequence SNPs were detected. Nor were any SNPs detected in probable splice signals. However, six SNPs were detected in the probable promoter of the gene. Two of these SNPs occur within 400 bp of the translation start site, while the others occur within approximately 0.9 kb, 1.2 kb and 1.3 kb of the translation start site. As a first approach to examining the possible functional impact of these SNPs, the 1.6 kb of sequence 5' to the ATG translation start site was compared to the TRASFAC database using the NSITE program available at the Sanger Centre web site. Three of the four SNPs occur in potential transcription factor binding sites. The most 3' of the sites (515b) lies at the base of a palindrome predicted to form an mRNA hairpin with a 14 bp stem. 5' UTR hairpins have been shown to function as translational regulatory elements. Although this analysis is speculative, it is consistent with this region being the promoter and a possible effect on transcription by these SNPs.

EXAMPLE 4

Linkage Disequilibrium Studies of GRK3

Sample 1 United States Triads

Four of the SNPs (e.g., 514a, 514b, 515a and 515b) identified in the GRK3 promoter region of the bipolar patients of Example 3 were examined for genetic association to bipolar disorder. In addition, four high frequency anonymous SNPs identified from the control subjects of Example 3 were also examined. Two of the latter SNPs are located 28 kb 5' to the GRK3 translation start site and two are located 110 and 150 kb 3' to the start of translation.

The seven single bp substitution SNPs were genotyped by the TaqMan allele specific assay method (Perkin Elmer) according to the manufacturer's protocols. For each site, primer pairs flanking the site to be interrogated were selected for PCR amplification of fragments of less than 150 bp. Two dual labelled probes centered on the SNP and differing in sequence by the one bp polymorphism of the SNP site itself were designed. The probes were labelled with 5' reporter fluors FAM or TET and 3' quencher TAMARA Sensitivity and specificity for allelic discrimination was tested over a wide range of primer and probe concentrations on the DNA samples whose allele type was previously determined. Concentrations and cycling parameters were chosen for genotyping that produced clustered values for heterozygotes which separated from homozygotes by greater than 4 standard deviations. Any samples which gave ambiguous calls were retyped. Accuracy of typing was checked by retyping 450 samples; no incorrect calls were detected. TaqMan reagents could not be developed for the 5'-UTR deletion variant (located at –130 bp). Instead this variant was typed by standard size-based methods commonly used for microsatellite genotyping. A FAM-labelled forward and unlabelled reverse primer pair were used to amplify a 228 bp genomic fragment spanning the variant. The one bp deletion was detected by size discrimination on a sequencing gel. All genotypes were read in a machine assisted fashion using ABI software and confirmed by two independent human readers.

Each SNP was genotyped in a set of 120 Caucasian pedigrees; 62 of these pedigrees consisted of parent and offspring trios and 58 pedigrees consisted of 2 or more siblings plus parents. In both types of families, the affected offspring were diagnosed with either bipolar I or bipolar II disorder. Therefore, there were a total of 181 triad families extracted from the 120 pedigrees. Allele frequencies for each of the markers in this set of pedigrees are listed in the Table 3. Transmission disequilibrium tests were carried out using the program TDT-LIKE (Terwilliger, *Am J Hum Genet* 56:777-787 [1995]). Using this program, transmitted and untransmitted alleles are counted from each heterozygote parent to an affected offspring. This method only counts transmissions where both parents have genotype information. Using TDTLIKE, a McNemar chi-square test statistic and associated one-sided p-values were computed. Two SNPs had nominal p-values less than 0.05. As shown in Table 3, allele "1" for marker 514a had 18 transmitted versus 5 untransmitted alleles (chi-square=7.34, p-value=0.007). In addition, allele "1" in marker 515a had 13 transmitted versus 4 untransmitted alleles (chi-square=4.8, p-value=0.03). P-values were also empirically computed using 10,000 replications as carried out using the program GASSOC v. 1.05 (Schaid, *Genet Epidemiol* 16:250-260 [1999]). The empirical p-values were similar to those derived from the chi-square statistic (p=0.009 for 514a, p=0.04 for A515a, respectively). With both markers, the associated allele had a frequency of less than 5 percent in this population. These results do show evidence for excess transmission in these two SNPs in the promoter region of GRK3 in this pedigree set. It must also be noted that the inclusion of multiple sibs in some of these families may make this in part a test of linkage, as well as linkage disequilibrium. Only six haplotypes for these four SNPs were observed (See, Table 4) indicating a high degree of linkage disequilibrium. As they are all in tight linkage disequilibrium, it is not possible to determine which of the three are most likely to be functionally relevant, or to exclude the possibility that the functional SNP is some other nearby variant not yet identified. However, analyses of the other SNPs approximately 40 kb upstream or 110 kb and 150 kb downstream were uniformly negative thereby bracketing the region for association to the vicinity of the promoter.

TABLE 3

TDT Analysis of GRK3 SNPs in Sample 1

| SNP | Location[1] | Allele[2] | Frequency | T[3] | N[3] | $\chi^2$ | p-value |
|---|---|---|---|---|---|---|---|
| A486a | –28 kb | 1 | 0.22 | 63 | 60 | 0.07 | n.s.[4] |
| A486b | –28 kb | 2 | 0.72 | 81 | 71 | 0.66 | n.s. |
| A514a | –1330 bp | 1 | 0.04 | 18 | 5 | 7.35 | 0.007 |
| A514b | –1306 bp | 1 | 0.99 | 5 | 4 | 0.11 | n.s. |
| A515a | –383 bp | 1 | 0.03 | 13 | 4 | 4.76 | 0.03 |
| A515b | –110 bp | 1 | 0.02 | 9 | 6 | 0.6 | n.s. |

TABLE 3-continued

TDT Analysis of GRK3 SNPs in Sample 1

| SNP | Location[1] | Allele[2] | Frequency | T[3] | N[3] | $\chi^2$ | p-value |
|---|---|---|---|---|---|---|---|
| A630 | 110 kb | 2 | 0.37 | 80 | 75 | 0.16 | n.s. |
| A665 | 150 kb | 2 | 0.45 | 85 | 82 | 0.05 | n.s. |

[1]Locations are relative to the translation start site.
[2]Alleles shown are those transmitted in excess to bipolar I/II offspring.
[3]Tranmitted (T) and Nontranmitted (N).
[4]Not significant (n.s.).

TABLE 4

GRK3 Promoter Haplotypes in Sample 1

| 514a | 514b | 515a | 515b | #[1] | T[2] | N[2] |
|---|---|---|---|---|---|---|
| + | | | | 5 | 4 | 1 |
| + | + | | | 2 | 2 | 0 |
| + | | + | | 9 | 6 | 2 |
| | | + | + | 1 | 1 | 0 |
| | | | + | 1 | 1[4] | 1[4] |
| | + | | | 8 | 5[4] | 5[4] |

[1]Number of heterozygous parents.
[2]Transmitted (T) and Nontransmitted (N).
[3]Indicates the presence of the less common sequence variant.
[4]Transmission of different alleles to each member of a sib pair.

Sample 2—Canadian Triads

As described above for the triads in Sample 1, two of the SNPs identified in the GRK3 promoter region of the bipolar patients of Example 3 were examined for genetic association to bipolar disorder in a second sample of 248 triads. The SNPs genotypes were SNPs 514a and 515a which are approximately 1300 and 300 bp upstream from the ATG, and about 100 and 1100 bp upstream from the approximate transcription start site. These SNPs yielded evidence of association to bipolar disorder in the first sample of 150 triads. SNPs 514a and 515a were genotyped using the TaqMan method and analyzed for association using the TDT. The results are summarized in Table 5.

TABLE 5

TDT Analysis of GRK3 SNPs in Sample 2

| | | Caucasian | | | | | | | |
|---|---|---|---|---|---|---|---|---|---|
| | | N. European (210) | | | | Non N. European (33) | | Non Caucasian (5) | |
| SNP | v[1] | T | N | $\chi^2$ | p value | T | N | T | N |
| 514a | 0.08 | 18 | 12 | 1.2 | n.s. | 2 | 4 | 0 | 2 |
| 515a | 0.04 | 10 | 3 | 3.8 | 0.05 | 2 | 3 | 1 | 2 |
| Haplotype | | | | | | | | | |
| 514a 515a | | | | | | | | | |
| + − | | 9 | 9 | | | 1 | 1 | 0 | 1 |
| + + | | 9 | 3 | | | 1 | 3 | 0 | 1 |
| − + | | 1 | 0 | | | 1 | 0 | 1 | 1 | v[1] indicates frequency

These results are consistent with those observed in Sample 1 which included both University of California, San Diego and National Institutes of Mental Health families. SNP 515a demonstrated an approximately three-fold greater rate of transmission compared to nontransmission (10:3). This resulted in a $\chi^2$ of 3.8 and a nominal p value of 0.05. In contrast to Sample 1 where SNP 514a gave the strongest results, it was non-significant in Sample 2. However, it is SNP 515a that is much closer to transcription initiation and therefore, more likely to be of functional consequence. These results were strongest in Caucasians of Northern European ancestry.

An analysis of the combined sample of 398 families is summarized below in Table 6. In families of Northern European ancestry, 515a was again the strongest with a $\chi^2$ of 8.5 and p value of 0.004, and an approximately 3 fold excess of transmission to non-transmission. However, 514a was also nominally significant with a $\chi^2$ of 6.8 and p value of 0.01.

TABLE 6

TDT Analysis of GRK3 SNPs in Samples 1 and 2

| | Caucasian | | | | | | | |
|---|---|---|---|---|---|---|---|---|
| | N. European (329) | | | | Non N. European (34) | | Non Caucasian (35) | |
| SNP | T | N | $X^2$ | p value | T | N | T | N |
| 514a | 36 | 17 | 6.8 | 0.01 | 2 | 5 | 5 | 7 |
| 515a | 23 | 7 | 8.5 | 0.004 | 2 | 3 | 4 | 5 |

EXAMPLE 5

GRK3 Protein Expression in Lymphoblastoid Cell Lines

In these experiments, GRK3 protein expression levels in cells from bipolar members of families with evidence of linkage to chromosome 22q11 and normal controls were tested. As GRK3 is expressed in lymphoblastoid cell lines, it is possible to measure levels of GRK3 message and protein directly in cell lines from patients most likely to have the mutation. Lymphoblastoid cells from bipolar I patients from the UCSD Bipolar Genetics Study cohort and normal controls were used at a similar degree of previous expansion (approximately passage 2 after immortalization with Epstein-Barr virus). Each bipolar patient came from a family with a lod score of >0.3 at D22S419 on chromosome 22.

Cells were grown in RPMI medium containing 10% fetal bovine serum and incubated at approximately 37° C., with 5% $CO_2$, to a cell density of $1 \times 10^6$ cells/ml. The cells were lysed in lysis buffer (20 mM Tris pH 7.5, 150 mM NaCl, 10 mM EDTA, 1% Triton-X 100, 1% sodium deoxycholate, 1 mM PMSF, 10 µg/ml benzamidine, 10 µg/ml leupeptin, 10 µg/ml soybean trypsin inhibitor, 5 µg/ml aprotinin, 1 µg/ml pepstatin A, 10 mM sodium pyrophosphate, 1 mM sodium orthovanadate, and 1 mM NaF).

The total gel protein was also determined. The protein concentration was determined using the Bradford method (Bio-Rad). Then, 100 µg of total cell lysates were resolved by SDS-PAGE on a 7% pre-cast gel (NuPAGE, Invitrogen-Novex), and transferred to PVDF membranes Invitrogen-Novex). The blot was incubated in the primary antibody at 4° C., overnight (anti-GRK3 goat polyclonal IgG, E-15, sc-9306, Santa Cruz, 1/200 dilution), and then with a horseradish peroxidase-conjugated second antibody (anti-goat HRP, sc-2033, Santa Cruz, 1/5000 dilution) for 1 hour. The bound antibodies were visualized by enhanced chemiluminescence, using the protocols recommended by the manufacturer (Amersham). The specificity of the antibody was verified by Western analysis using purified GRK2 and GRK3 proteins. The molecular weight of the detected bands was consistent with that of the purified protein.

Figure 3:
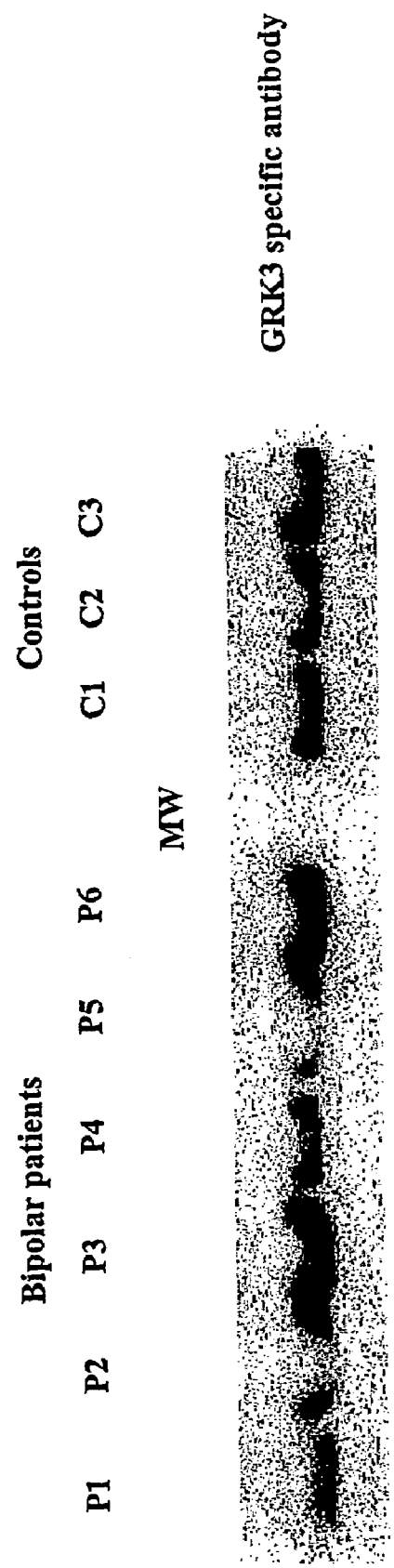
FIG. 3 shows a Western blot of cell lysates from bipolar patients and normal controls, probed with a GRK3-specific antibody (sc-9306). Similar amounts of protein were run in each lane as confirmed by Coomassie staining of an identical gel (not shown).

FIG. 3 shows a Western blot in which an antibody specific for GRK3 was used (sc-9306). In this Figure, "bipolar" indicates bipolar members of families with linkage to chromosome 22q11, while "control" indicates normal controls. The "mw" indicates the lane containing molecular weight standards. A significant decrease in GRK3 was observed in 3 out of 6 probands, as compared to controls. Three additional control subjects were examined on a separate blot (not shown) and demonstrated GRK3 levels comparable to that of the controls shown in FIG. 3.

EXAMPLE 6

GRK3 Protein Expression in Brain Derived Cell Lines

A neuroblastoma cell line (SK-N-MC) that endogenously expresses GRK3 and demonstrates desensitization to dopamine stimulation has been identified as a suitable model system for studies of transcriptional regulation. A separate sets of PCR primers specific to GRK2 and for GRK3, that span a 300 bp region including exons 11 and 12, have been developed. cDNAs for GRK2 and for GRK3 were separately and specifically amplified by RT-PCR from SK-N-MC cells and confirmed by sequencing. The endogenous expression of GRK3 in SK-M-MC was further confirmed by immunoblotting cell lysates and probing them with a mouse monoclonal antibody that recognizes both GRK2 and GRK3 [C5/1 1:1000] (Dautzenberg et al., *Am J. Physiol.* [2001]; and Dautzenberg and Hauger, *Neurophamiacology* [2001]). ECL+Plus detection was performed (Amersham) and blots analyzed on the STORM imager using ImageQuant software (Molecular Dynamics).

Figure 4:
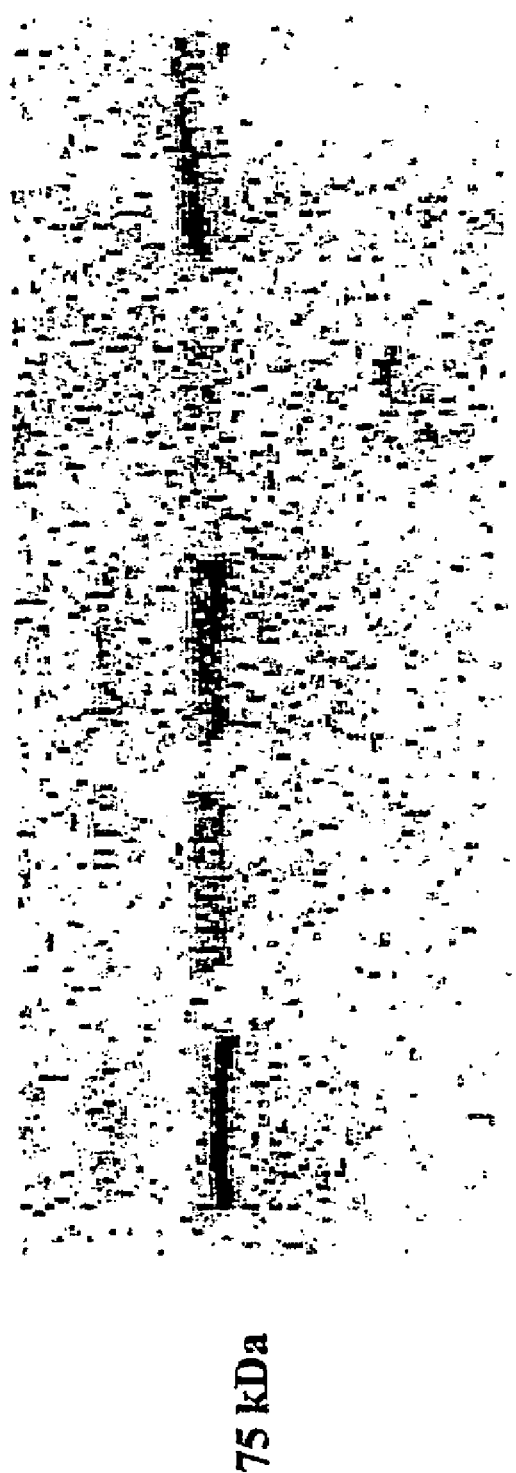
FIG. 4 shows a Western blot of cell lysates from several brain-derived cell lines, probed with a GRK3-specific antibody. The cell lines used in this study included retinoblastoma (Y-79) cells, neuroblastoma (SK-N-MC) cells, and amygdalar (AR-5) cells.

As shown in FIG. 4, GRK3 protein was detected in both SK-N-MC cells and in a retinoblastoma (Y79) cell line. Blots were run with purified protein standards for GRK3 and GRK2 that migrated to ~78 kD and ~80 kD, respectively, the known molecular weights of these kinases. Well-defined SK-N-MC and Y79 cell lysate bands that migrated to a position parallel to the GRK3 standard were identified as GRK3 protein. However, no immunoreactive bands in these two cell lines were detected at the position of the GRK2 standard. In addition, GRK2 and GRK3 protein were not detected in rat amygdalar AR5 cells Mulchahey et al., *Endocrinology* 140:251-259 [1999]). The use of other GRK2-specific and GRK3-specific polyclonal and monoclonal antibodies is also contemplated (Dautzenberg et al., *Am J. Physiol.* [2001]; Dautzenberg and Hauger, *Neuropharmacology* [2001]; and Oppermann et al., *Proc Natl Acad Sci USA* 93:7649-7654 [1996]).

EXAMPLE 7

Identification of the GRK3 Transcription Start Site

Two principal kinds of evidence indicate that it is very likely that GRK3 transcription is initiated within the ~1,600 base pairs of upstream sequence that has been examined in Example 3. First, the GRK3 upstream sequences strongly resemble those of the closely related gene GRK2. For GRK2, the region immediately 5' to the first exon has been shown to contain multiple transcriptional start sites (Penn and Benvic, *J Biol Chem* 269:14924-14930 [1994]). In the GRK2 work, a major transcription start site was identified at –245 bp relative to the ATG at which translation is initiated, plus 6 additional minor starts from –47 to –232 bp. In addition, this region has been shown to have promoter activity in multiple cell types that express GRK2 endogenously (Ramos-Ruiz et al., *Circulation* 101:2083-2089 [2000]). Second, both GRK2 and GRK3 have similar GC-rich regions within 0.5 kb upstream from the start of their open reading frames, strongly suggestive of SP1 sites typically associated with transcriptional initiation in promoters lacking TATA elements. In GRK3, these GC-rich regions extend from about 500 bp upstream of the ATG of the first coding exon through the first exon itself. The domain from –500 bp through –200 bp has ~75% GC content, the next 200 bp consists of ~90% GC, and the first 113 bp of the open reading frame are ~70% GC. Therefore, by analogy to GRK2 and from the presence of typical elements associated with transcriptional initiation, GRK3 transcription is likely to start within ~500 bp of the open reading frame.

A human neuroblastoma cell line (SK-N-MC) that endogenously expresses GRK3 is used for functional studies of GRK3 expression. The first approach contemplated for the identification of transcription start sites involves amplifying and sequencing the 5' end of the GRK3 mRNA by a "run-off" reverse transcription reaction. This approach permits the length and identity of the 5' end of the transcript to be determined and indicates whether the first coding exon is truly the first exon of the gene or whether there is an additional upstream intron. Using the "rapid amplification of cDNA ends" (RACE) procedure (GIBCO BRL), a GRK3 gene specific reverse primer and a high temperature reverse transcriptase (ThermoScript, GIBCO BRL) are used to make a cDNA copy of the 5' end of the GRK3 mRNA. This cDNA is tailed with oligo-dC using terminal transferase, and amplified with the GIBCO BRL forward anchor (poly T) primer and a nested GRK3 gene specific primer. The product is then either sequenced directly, or cloned into a suitable vector (GIBCO BRL).

To confirm that the cDNA end identified by RACE is indeed the mRNA terminus, RNase protection assays are contemplated. Riboprobes are prepared from overlapping, ~300 bp fragments of the GRK3 promoter region immediately upstream of and encompassing the putative transcription start sites, which have been cloned into a T7/T3 transcription vector. A series of RNase protection assays are conducted in order to identify the 5' extent of exon one. True sites for transcription initiation are confirmed by the coincidence of the 5' end of the RACE clones and the 5' extent of RNase protection.

Further confirmation and information regarding the approximate length of GRK3 mRNAs are obtained by performing a Northern blot on RNA from SK-N-MC cells. A Northern, published in 1991 (Benovic et al. *FEBS Lett* 283: 122-126 [1991], indicated a major transcript of 8 kb. The Sanger Centre database predicts polyA sites which would yield mRNAs of ~2500, ~3500, and ~7500 bp. Because the open reading frame encompasses only 2064 bp, the presence of an abundant 2500 bp transcript places the location of the transcription start site within the expected upstream region. If longer transcripts are present, information from the Northern does not definitively confirm data from the other studies, but provides useful information regarding message size and processing.

EXAMPLE 8

GRK3 Promoter Studies

In this Example, methods for examining GRK3 promoter function are described. A 1.5 kb region was amplified from DNA from a subject lacking the promoter SNPs described in Example 3. This region extended from approximately 20 bp upstream of the ATG to –1.5 kb. Restriction sites placed on the primers were used to ligate this product into the multiple cloning site of the pGL3 Basic vector (Promega). This vector includes a firefly luciferase open reading frame downstream from the multiple cloning site, and is designed for transfection studies of promoter function. In addition to this construct, pGL3 Basic without insert was used as a negative control and a pGL3 construct with a SV40 promoter and enhancer was used as a positive control. These constructs were incubated at a 2:1 ratio of 2 µl Superfect (Stratagene) to 1 µg DNA for 10 minutes. This mixture was then added to plates of SK-N-MC neuroblastoma cells for two hours per the manufacturer's recommendations. The medium was then changed and the incubation continued for 24 hours at which time the cells were lysed and luciferase activity measured in a luminometer. Each experiment was conducted in five replicate plates.

As shown in Table 7, the pGL3 construct with the GRK3 promoter showed a 5-8 fold increase in luciferase activity over the pGL3 Basic null vector. These results are consistent with this region having promoter function for the GRK3 gene and are similar to results reported for the GRK2 promoter which showed an approximately 10-20 fold increase in activity. The use of transfection efficiency controls such as β-galactosidase or *Renilla* luciferase is contemplated. Testing the promoter activity of a series of 5'-deletions of variable length spanning this region, is contemplated to define the minimal region necessary to confer transcriptional activity.

TABLE 7

Results of Transfection Experiments

| Vector | Relative Luciferase Activity |
|---|---|
| pGL3 Basic | 1 |
| pGL3 + 1.5 kb GRK3 promoter | 5-8 |
| pGL3 + SV40 promoter and enhancer | 300-600 |

A comparison of the relative transcriptional function of the variant GRK3 haplotypes is also contemplated. Reporter constructs are made for each of the six observed GRK3 promoter SNP haplotypes. This is accomplished by PCR amplification of the 1.6 kb region from genomic DNA of subjects known to have each haplotype. Each construct is sequenced to verify that it contains the desired haplotype. Each of these constructs is transfected into SK-N-MC cells in triplicate, in parallel with the consensus haplotype. Luciferase assays are conducted in triplicate, normalized to the expression of a co-transfected β-galactosidase or *Renilla* luciferase expression plasmid, and compared by analysis of variance.

EXAMPLE 9

Nuclear Protein Binding

In vitro studies of protein-DNA interaction provide a second avenue for examining the functional significance of the GRK3 promoter region SNPs. Specifically, extracts from cells which express GRK3 are suitable for use in the analysis of differences in DNA binding between the consensus and mutant alleles. The two widely used in vitro methods for examining the interaction of cellular transcription factors with potential regulatory elements in target DNA sequences are DNaseI footprinting and electrophoretic mobility shift assays (EMSAs). Because the present work focuses on the transcriptional effect of four discrete single base-pair variants in the GRK3 regulatory region, EMSA assays are the method of choice in these experiments.

For these assays, 30 base-pair double-stranded oligonucleotides containing the consensus and variant form of each SNP are synthesized. The base-pair containing the SNP is centered in the oligonucleotide sequence, and the length chosen is sufficient to provide recognition sites for a wide variety of monomeric and dimeric transcription factors. The four consensus and 4 variant oligonucleotides are radiolabelled, and EMSA assays performed in the presence of poly-dI/dC, using standard methods extensively applied to the analysis of neural transcription factors (Gruber et al., *Mol Cell Biol* 17:2391-2400 [1997]; and Trieu et al., *J Neurosci* 19:6549-6558 [1999]). It is contemplated that in some cases, for each oligonucleotide sequence, these assays reveal one or several protein-DNA complexes, which appear as slower-migrating bands in polyacrylamide gels. If the consensus and variant GRK3 alleles have different transcription factor binding properties, these are revealed in qualitative or quantitative differences in the pattern of shifted bands. Specific binding is verified by conducting parallel assays in the presence of a 50-fold excess of unlabelled oligonucleotide.

In principle, these EMSA assays are suitable for the assessment of whether the transcription factor pool of any cell type can discriminate between the GRK3 consensus and variant promoter sequences. Clearly, however, this is only of biological interest in cells that express GRK3 endogenously. Thus, this EMSA analysis is applied initially to cellular extracts from SK-N-MC cells, and SK-N-MC cells that have been treated with dopamine. Cellular extracts are prepared by previously described methods (Carter, *Biochem Biophys Res Commun* 166:589-594 [1990]; and Kelsoe et al., *Nature* 342: 238-243 [1989]). Extracts of other cell lines that strongly express GRK3 are also suitable for use in these assays. The immediate goal of EMSA analysis is to demonstrate differential binding of transcription factors to oligonucleotides containing one or more of the GRK3 promoter variants. To test whether differences in EMSA assays reveal transcriptionally significant effects, a single copy and 3× concatamers of the consensus and variant oligonucleotides are linked to a minimal promoter in the pGL3 reporter system (Gruber et al., supra [1997]), and compared in transfection assays in SK-N-MC cells. It is contemplated that examination of transcriptional activity in this controlled context will reveal functional differences that are obscured in the context of the entire 1.6 kb promoter region.

It is also possible to obtain some insight into which transcription factors account for the mobility shifts of the GRK3 derived oligonucleotides through the examination of DNA sequences. For instance, SNP 514b alters a predicted binding site for the ubiquitous transcriptional regulator SP1 (See, FIG. 2). However, the ability to predict specific transcription factor binding sites from DNA sequence data is presently rudimentary. Recently, biotechnology companies have made a substantial effort to market antisera to a wide range of transcription factors (CeMines, Santa Cruz Biotechnology). These antibodies can be used to "supershift" EMSA complexes in polyacrylamide gels. By narrowing the list of candidate factors using sequence data, then applying these specific reagents, these methods provide a strong possibility of identifying the transcriptional regulators that interact with the polymorphic GRK3 sequences. More general methods, such as expression screening of phage libraries (e.g., those derived from SK-N-MC cells), and one-hybrid screening in yeast, allow the cloning and identification of DNA binding factors identified by EMSA assays for which no specific antisera exist.

EXAMPLE 10

Allele Specific Transcript Quantification

As discussed in greater detail above, the transfection experiments of Example 7 examine the function of a relatively short region of the GRK3 regulatory sequence. This determines the functional significance of the polymorphisms within this region. However, it is possible that additional upstream variants contribute to the phenotype and are in linkage disequilibrium with the detected polymorphisms. In this case, the true functional mutations would be overlooked in some transfection studies. This intrinsic limitation of the transfection assays can be overcome if the transcripts from the genomic consensus and variant alleles can be distinguished in GRK3-expressing cells from heterozygous patients, yielding an assay of allele-specific gene expression. In a subset of subjects, SNP 515b, which is very likely to reside within the GRK3 5'-UIR, allows such an assay to be performed. Measuring the ratio of allele-specific GRK3 expression within a cell line also has the advantage of comparison against a naturally occurring internal control, thereby eliminating differences in expression resulting from a variety of factors ranging from the subject's medical or treatment history or age, to transformation by EBV and subsequent expansion in culture. It is contemplated that SNP 515b affects a translational regulation element, and that it is a functional SNP. Means to determine this possibility are provided by the transfection studies described in Example 7. Even if SNP 515b does affect translational regulation, the approach described herein is suitable for testing of additional differences in transcriptional regulation, as only differences in mRNA levels are examined.

As discussed in Example 5, GRK3 is expressed in lymphoblastoid cell lines. Thus, cell lines from patients who carry SNP 515b are suitable for use for allele-specific GRK3 expression. As shown in Table 4, the haplotype with variants at sites 514a, 515a and 515b is the most common variant haplotype in the 110 families. At present, 18 subjects heterozygous for this most common variant haplotype (514a/515a/515b, nine parents and nine of their offspring), one subject heterozygous for sites 515a/515b, and four subjects heterozygous for 515b only, have been identified. The use of an allele specific expression assay, based on single base pair extension (SBE) is contemplated. mRNA from the cell line being interrogated is DNase I treated, reverse transcribed using ThermoScript (GIBCO BRL) and a GRK3 specific primer, then a 238 bp fragment containing the 515b SNP is amplified by PCR using primers already proven by sequencing to produce a GRK3 specific product. SBE primers are designed which terminate one bp proximal to the 515b variant. Since the variant is a one bp deletion (See, FIG. 2), a single base addition using ddCTP and ddGTP labelled with different fluorescent tags adds a G to the wild type allele, but C to the variant that is distinguishable by fluorescent color. Primers fluorescently labelled by the single base extension reaction are separated from unincorporated nucleotides and the fluorescent intensity produced by the G vs. C fluors is determined on an ABI 7700. The ratio of fluor intensities is used to quantify haplotype specific expression. Validity of the system and signal intensities produced from a true 50:50 ratio of variant to wild type starting material is determined by two techniques. First, the two species of RNA are produced from riboprobe vectors, carefully quantitated, and mixed at a 1:1 ratio, then tested. Second, the PCR and SBE steps of the system are tested on genomic DNA from homozygous wild type vs. heterozygous individuals.

Patient lymphoblastoid cell lines from subjects heterozygous for each of the three haplotypes are thawed and grown under controlled conditions, so as to assure a similar degree of expansion, cell density ($10^6$ cells/ml) and growth conditions. Allele specific expression is then determined as described above. Each measurement is conducted in triplicate and differences assessed by ANOVA.

As discussed in regards to the transfection studies, it is possible that the effect of some promoter variants will only be manifest when the system is challenged to turn on expression. Thus, it is contemplated that patient lymphoblastoid cell lines provide a system which can be pharmacologically challenged for additional assessment of promoter function. Preliminary experiments suggest that lymphoblastoid cell lines do not express dopamine receptors. However, they are well known to express β-adrenergic receptors, generate cAMP in response to βagonists, and to desensitize in response to prolonged treatment (Yu et al., *Neuropsychopharmacol* 21:147-152 [1999]; Wright et al., *Ann Hum Genet* 48:201-214 [1984]). It is contemplated that GRK3 mediates this desensitization. If a difference in allele specific expression is not demonstrated in unchallenged cells, RT-PCR experiments are conducted to determine if GRK3 mRNA levels are induced by the β agonist, isoproterenol. If so, then further experiments are conducted to determine the dose response curve and time course, in order to choose optimal conditions for maximal stimulation of GRK3 expression. Then, SNP 515b is used in similar fashion and with the same cell lines described above to examine haplotype specific transcription in pharmacologically challenged lymphoblastoid cell lines.

EXAMPLE 11

Screening for Additional Mutations

As described in Example 9, it is contemplated that the SNPs identified in the 1.6 kb upstream region are not the functional SNPs themselves, but rather in linkage disequilibrium with the actual functional variants that are located elsewhere in the gene. The allele specific expression experiments in patient lymphoblastoid cell lines described above are designed to detect such a possibility. In addition to these functional expression experiments, the identification by sequencing of additional functional variants is contemplated.

The challenge of such a problem is the large size of the genomic regions that could potentially be involved. Enhancer or repressor elements have been identified in some genes tens of kb upstream from transcription initiation. Similarly, many genes with large first introns, such as GRK3, have regulatory elements in intron 1. The target is somewhat bracketed by the negative linkage disequilibrium results from flanking SNPs. These data indicate that the functional regulatory SNPs are likely between −30 kb and +100 kb of the ATG. However, this is still an enormous area Thus the use of evolutionary conservation of regulatory sequence is contemplated as a guide in selecting regions to sequence. Transcriptional regulatory elements are frequently highly conserved across a wide range of species. Therefore, it is contemplated that non-coding sequences conserved between mouse and human in the vicinity of the GRK3 gene reflect conserved regulatory elements, and will find use in guiding sequencing efforts. Mouse and human genomic sequences from −50 kb upstream of the ATG to 50 kb 3' of the last exon are compared using BLAST algorithms and by eye. Conserved regions are prioritized based on the degree of sequence conservation, and correspondence to known transcription factor consensus sequences in the TRANSFAC database (using the NSITE program on the Sanger Centre web page). These regions are screened by sequencing in subjects with bipolar disorder using the same approach and methods employed in the identification of the four promoter SNPs already identified.

Primers are designed so as to amplify PCR products from genomic regions of approximately 300 bp around each conserved region. These regions are amplified from the same 14 subjects studied previously whose families have positive lod scores at the marker D22S419 near the GRK3 gene. Fragments are sequenced bidirectionally using the Perkin Elmer Big Dye fluor-ddNTP sequencing kit and an ABI 377 sequencer, per the manufacturer's recommendations. Minor modifications are used for sequencing GC-rich regions such as those around the promoter (e.g., annealing temperature of 54° C. and addition of 5% DMSO). Sequencing gels are tracked and data extracted using ABI sequence analysis software.

Chromatogram files are then transferred to a Sun UNIX workstation for assembly into contigs using the Pred/Phrap/ Consed suite of programs and SNPs will be identified using PolyPhred and by visual inspection. All promoter and exon sequences are visually scanned to evaluate sequence quality, confirm SNPs, and check for possible false negatives (i.e., missed SNPs). Likewise, any regions of reduced sequence quality (<30 on the Pred/Phrap scale, or an approximate error rate of 1:1000) are visually inspected and resequenced, if necessary. SNPs identified in this fashion are genotyped in the triad sample and tested for linkage disequilibrium to bipolar disorder. SNPs that demonstrate genetic association to bipolar disorder are tested for functional impact using the same general approaches described for the promoter SNPS.

EXAMPLE 12

Screening of Compounds

In this Example, methods for screening compounds that increase the expression and function of psychosis-suppressor genes and/or decrease the expression and function of psychogenes in the basal state and preferably in the presence of an appropriate agonist are provided. In one particular embodiment, compounds that increase the action of GRK3 in both the basal and agonist-challenged states are identified. However, it is not intended that the present invention be limited to compounds that impact the function and/or expression of GRK3, as it is contemplated that the present invention will find use in screening and identifying various other compounds. It is further intended that the present invention will find use with other genes and compounds that affect their expression. Thus, it is not intended that the present invention will be limited to GRK3 and/or dopamine or any other neurotransmitter, agonist, and/or pharmacological compound (i.e., it is contemplated that any appropriate compound will find use in the present invention).

In these particular experiments, lymphoblastoid cells obtained from normal control subjects, and subjects with bipolar disorder (e.g., with a genetic defect in GRK3) are grown and maintained as described in Example 5. As these cells express GRK3, adenylate cyclase, and the necessary G proteins, they are contemplated as being particularly useful in these methods. The cells are tested "unchallenged" (i.e., without dopamine agonist) as well as "challenged" (i.e., in the presence of a dopamine agonist). Various concentrations of dopamine and the compound are tested in each of these experiments. The cells are tested for the level of GRK3 mRNA expression, GRK3 protein expression, D1 receptor phosphorylation, and cAMP production. In the presence of the dopamine agonist, compounds of particular interest increase GRK3 mRNA expression, GRK3 protein expression, and D1 receptor phosphorylation, and decrease cAMP production.

In additional experiments, the cell lines are challenged with at least one beta adrenergic agonist. Thus, in these experiments, the cells are tested with various compounds in the presence or absence of beta adrenergic agonist(s), to determine the ability of the test compounds to modulate GRK3 function. Thus, as with tests including dopamine agonists, in these tests, compounds of particular interest increase GRK3 mRNA expression, GRK3 protein expression, and D1 receptor phosphorylation, and decrease cAMP production.

These screening methods need not be limited to lymphoblastoid cell lines. In preferred embodiments, neurally derived cell lines (i.e., SK-N-MC) are used. In addition, the screening methods of the invention need not be limited to measurement of endogenous GRK3. In fact, the use a reporter construct designed to express luciferase or green fluorescent protein from a GRK3 promoter is contemplated. Such an assay includes a dopamine agonist, a neurally derived cell line transfected with a GRK3 reporter construct, and the test compound. The effect of the test compound on GRK3 expression is measured by quantitating light or fluorescence output.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art and/or related fields are intended to be within the scope of the following claims.

What is claimed is:

1. A method for assessing susceptibility to bipolar disorder comprising detecting sequence variation in at least one fragment of a G protein-coupled receptor kinase 3 gene of a Caucasian human subject, wherein said sequence variation comprises a guanine to adenine transition at a nucleotide corresponding to position 1180 of SEQ ID NO:1, and wherein the presence of said sequence variation is associated with increased susceptibility to bipolar disorder.

2. The method of claim 1, wherein said detecting comprises nucleotide sequencing.

3. The method of claim 1, wherein said subject is at risk of developing bipolar disorder.

4. The method of claim 1, wherein said Caucasian human subject is of northern European descent.

5. The method of claim 1, wherein said detecting comprises a PCR assay utilizing 5' nuclease activity of Taq polymerase to cleave an allele-specific fluorescently-labelled probe.

6. A method for genotyping a Caucasian human subject comprising detecting one or more single nucleotide polymorphisms (SNPs) in a G-protein coupled receptor kinase 3 (GRK3) gene in a sample obtained from said Caucasian human subject, wherein the one or more SNPs is selected from the group consisting of T233C, A257G, G1180A, and G1453 deletion, of the GRK3 sequence of SEQ ID NO: 1, wherein said detecting comprises a PCR assay utilizing 5' nuclease activity of Taq polymerase to cleave an allele-specific fluorescently-labelled probe.

* * * * *